(12) United States Patent
Addison et al.

(10) Patent No.: US 8,755,854 B2
(45) Date of Patent: Jun. 17, 2014

(54) METHODS AND APPARATUS FOR PRODUCING AND USING LIGHTLY FILTERED PHOTOPLETHYSMOGRAPH SIGNALS

(75) Inventors: Paul Stanley Addison, Edinburgh (GB); James Watson, Dunfermline (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1010 days.

(21) Appl. No.: 12/533,239

(22) Filed: Jul. 31, 2009

(65) Prior Publication Data
US 2011/0028802 A1    Feb. 3, 2011

(51) Int. Cl.
| A61B 5/1455 | (2006.01) |
| A61B 5/145 | (2006.01) |
| A61B 5/00 | (2006.01) |

(52) U.S. Cl.
CPC .......... *A61B 5/1455* (2013.01); *A61B 5/14552* (2013.01); *A61B 5/14532* (2013.01); *A61B 5/0059* (2013.01)
USPC ...................................................... 600/310

(58) Field of Classification Search
CPC .................................................... A61B 5/1455
USPC ................ 600/310, 323, 330, 504
See application file for complete search history.

(56) References Cited

U.S. PATENT DOCUMENTS

| 3,532,087 A | 10/1970 | Horn |
| 3,884,219 A | 5/1975 | Richardson et al. |
| 3,926,177 A | 12/1975 | Hardway et al. |
| 4,289,141 A | 9/1981 | Cormier |
| 4,696,307 A | 9/1987 | Montgieux |
| 5,143,078 A | 9/1992 | Mather |
| 5,273,036 A | 12/1993 | Kronberg |
| 5,439,483 A | 8/1995 | Duong-Van |
| 5,575,284 A | 11/1996 | Athan |
| 5,590,650 A | 1/1997 | Genova |
| 5,632,272 A | 5/1997 | Diab et al. |
| 5,680,871 A | 10/1997 | Ganshorn |
| 5,682,898 A | 11/1997 | Aung |

(Continued)

FOREIGN PATENT DOCUMENTS

| JP | 09-084776 | 3/1997 |
| JP | 1997-084776 | * 3/1997 |

(Continued)

OTHER PUBLICATIONS

Addison, Paul S., The Illustrated Wavelet Transform Handbook, Taylor & Francis Group, 2002.

(Continued)

*Primary Examiner* — Clayton E Laballe
*Assistant Examiner* — Kevin Butler
(74) *Attorney, Agent, or Firm* — Shvarts & Leiz LLP

(57) ABSTRACT

One or more physiological conditions of a patient can be observed by obtaining a photoplethysmograph ("PPG") signal from the patient and by only lightly filtering that signal. The light filtering of the PPG may be such as to only remove (for example) high frequency noise from that signal, while leaving in the signal most or all frequency components that are due to physiological events in the patient. In this way, such physiological events can be observed via a visual display of the lightly filtered PPG signal and/or via other signal processing of the lightly filtered PPG signal to automatically extract certain physiological parameters or characteristics from that signal.

22 Claims, 18 Drawing Sheets

(56) References Cited

U.S. PATENT DOCUMENTS

| | | | |
|---|---|---|---|
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,142,953 A | 11/2000 | Burton | |
| 6,171,257 B1 | 1/2001 | Weil et al. | |
| 6,171,258 B1 | 1/2001 | Karakasoglu et al. | |
| 6,208,951 B1 | 3/2001 | Kumar et al. | |
| 6,293,915 B1 | 9/2001 | Amano et al. | |
| 6,325,761 B1 | 12/2001 | Jay | |
| 6,361,501 B1 | 3/2002 | Amano et al. | |
| 6,363,270 B1 | 3/2002 | Colla et al. | |
| 6,393,311 B1 | 5/2002 | Edgar, Jr. et al. | |
| 6,398,727 B1 | 6/2002 | Bui et al. | |
| 6,463,311 B1 | 10/2002 | Diab | |
| 6,561,986 B2 | 5/2003 | Baura | |
| 6,606,511 B1 | 8/2003 | Ali et al. | |
| 6,608,934 B2 | 8/2003 | Scheirer | |
| 6,654,623 B1 | 11/2003 | Kastle | |
| 6,658,276 B2 | 12/2003 | Kianl et al. | |
| 6,684,090 B2 | 1/2004 | Ali et al. | |
| 6,702,752 B2 | 3/2004 | Dekker | |
| 6,709,402 B2 | 3/2004 | Dekker | |
| 6,801,798 B2 | 10/2004 | Geddes et al. | |
| 6,810,277 B2 | 10/2004 | Edgar, Jr. et al. | |
| 6,811,538 B2 | 11/2004 | Westbrook et al. | |
| 6,896,661 B2 | 5/2005 | Dekker | |
| 6,918,878 B2 | 7/2005 | Brodnick | |
| 6,930,608 B2 | 8/2005 | Grajales et al. | |
| 6,931,269 B2 | 8/2005 | Terry | |
| 6,990,426 B2 | 1/2006 | Yoon et al. | |
| 7,001,337 B2 | 2/2006 | Dekker | |
| 7,020,507 B2 | 3/2006 | Scharf | |
| 7,035,679 B2 | 4/2006 | Addison | |
| 7,043,293 B1 | 5/2006 | Baura | |
| 7,052,469 B2 | 5/2006 | Minamiura et al. | |
| 7,054,453 B2 | 5/2006 | Causevic | |
| 7,054,454 B2 | 5/2006 | Causevic et al. | |
| 7,079,888 B2 | 7/2006 | Oung | |
| 7,171,251 B2 | 1/2007 | Sarussi | |
| 7,171,269 B1 | 1/2007 | Addison | |
| 7,173,525 B2 | 2/2007 | Albert | |
| 7,203,267 B2 | 4/2007 | De Man et al. | |
| 7,225,013 B2 | 5/2007 | Geva et al. | |
| 7,246,618 B2 | 7/2007 | Habashi | |
| 7,254,500 B2 | 8/2007 | Makeig | |
| 7,289,835 B2 | 10/2007 | Mansfield | |
| 7,309,314 B2 | 12/2007 | Grant et al. | |
| 7,344,497 B2 | 3/2008 | Kline | |
| 7,381,185 B2 | 6/2008 | Zhirnov et al. | |
| 7,398,115 B2 | 7/2008 | Lynn | |
| 7,421,296 B1 | 9/2008 | Benser | |
| 7,515,949 B2 | 4/2009 | Norris | |
| 7,519,488 B2 | 4/2009 | Fu | |
| 7,523,011 B2 | 4/2009 | Akiyama et al. | |
| 7,944,551 B2 | 5/2011 | Addison et al. | |
| 8,295,567 B2 | 10/2012 | Watson et al. | |
| 2003/0163057 A1 | 8/2003 | Flick et al. | |
| 2003/0212336 A1* | 11/2003 | Lee et al. | 600/504 |
| 2005/0022606 A1 | 2/2005 | Partin et al. | |
| 2005/0043616 A1 | 2/2005 | Chinchoy | |
| 2005/0109340 A1 | 5/2005 | Tehrani | |
| 2005/0215915 A1 | 9/2005 | Noda et al. | |
| 2005/0222502 A1 | 10/2005 | Cooper | |
| 2005/0251056 A1 | 11/2005 | Gribkov et al. | |
| 2006/0074333 A1 | 4/2006 | Huiku | |
| 2006/0155206 A1 | 7/2006 | Lynn | |
| 2006/0173257 A1 | 8/2006 | Nagai et al. | |
| 2006/0209631 A1 | 9/2006 | Melese et al. | |
| 2006/0211930 A1 | 9/2006 | Scharf et al. | |
| 2006/0217603 A1 | 9/2006 | Nagai et al. | |
| 2006/0229519 A1 | 10/2006 | Fujiwara et al. | |
| 2006/0241506 A1 | 10/2006 | Melker et al. | |
| 2006/0258921 A1 | 11/2006 | Addison et al. | |
| 2006/0265022 A1 | 11/2006 | John et al. | |
| 2006/0282001 A1 | 12/2006 | Noel et al. | |
| 2007/0015976 A1 | 1/2007 | Miesel et al. | |
| 2007/0021673 A1 | 1/2007 | Arbel et al. | |
| 2007/0073120 A1 | 3/2007 | Li et al. | |
| 2007/0073124 A1 | 3/2007 | Li et al. | |
| 2007/0129647 A1 | 6/2007 | Lynn | |
| 2007/0149883 A1 | 6/2007 | Yesha | |
| 2007/0167694 A1 | 7/2007 | Causevic et al. | |
| 2007/0167851 A1 | 7/2007 | Vitali et al. | |
| 2007/0282212 A1 | 12/2007 | Sierra et al. | |
| 2008/0045832 A1 | 2/2008 | McGrath | |
| 2008/0060138 A1 | 3/2008 | Price et al. | |
| 2008/0076992 A1 | 3/2008 | Hete et al. | |
| 2008/0082018 A1 | 4/2008 | Sackner et al. | |
| 2008/0171946 A1 | 7/2008 | Hansmann | |
| 2008/0190430 A1 | 8/2008 | Melker et al. | |
| 2008/0202525 A1 | 8/2008 | Mitton et al. | |
| 2008/0214903 A1 | 9/2008 | Orbach | |
| 2008/0243021 A1 | 10/2008 | Causevic et al. | |
| 2009/0326402 A1 | 12/2009 | Addison et al. | |
| 2010/0286495 A1* | 11/2010 | McGonigle et al. | 600/330 |

FOREIGN PATENT DOCUMENTS

| | | |
|---|---|---|
| WO | WO 00/21438 | 4/2000 |
| WO | WO 01/25802 | 4/2001 |
| WO | WO 01/62152 | 8/2001 |
| WO | WO 01/76471 | 10/2001 |
| WO | WO 03/000125 | 1/2003 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |
| WO | WO 2008/043864 | 4/2008 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2005, pp. 1-24.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, vol. 20, No. 1, 2006, pp. 33-36.

Leonard, Paul A., Clifton, David, Addison, Paul S., Watson, James N., Beattie, Tom "An Automated Algorithm for Determining Respiratory Rate by Photoplethysmogram in Children," Acta Paediatrica, 2006; 95: 1124-1128.

Yamada, Michio, "Wavelet Analysis and Its Application," Journal of the Institute of Electronics, Information and Communication Engineers, vol. 76, No. 5, May 1993, pp. 518-528.

* cited by examiner

METHODS AND APPARATUS FOR PRODUCING AND USING LIGHTLY FILTERED PHOTOPLETHYSMOGRAPH SIGNALS

CROSS REFERENCE TO RELATED APPLICATIONS

Portions of this specification will also be found in Addison et al. U.S. patent application Ser. No. 12/245,366, filed Oct. 3, 2008, which is hereby incorporated by reference herein in its entirety.

SUMMARY OF THE DISCLOSURE

The present disclosure relates to signal processing and, more particularly, the present disclosure relates to using continuous wavelet transforms for processing, for example, a photoplethysmograph (PPG) signal, to determine effort, such as respiratory effort of a patient.

Systems and methods to analyze the suitable signal domain representation in order to determine effort are disclosed herein. In one embodiment, effort may relate to a measure of strength of at least one repetitive feature in a signal. In another embodiment, effort may relate to physical effort of a process that may affect the signal (e.g., effort may relate to work of a process).

In some embodiments, the use of a transform may allow a signal to be represented in a suitable domain such as, for example, a scalogram (in a time-scale domain) or a spectrogram (in a time-frequency domain). A type of effort which may be determined by analyzing the signal representation may be, for example, breathing effort of a patient. The breathing effort of the patient may be determined by analyzing a scalogram with the processes presented in this disclosure.

The determination of effort from a scalogram or any other signal representation is possible because changes in effort induce or change various features of the signal used to generate the scalogram. For example, the act of breathing may cause a breathing band to become present in a scalogram that was derived from a PPG signal. This band may occur at or about the scale having a characteristic frequency that corresponds to the breathing frequency. Furthermore, the features within this band or other bands on the scalogram (e.g., energy, amplitude, phase, or modulation) may result from changes in breathing and/or breathing effort and therefore may be correlated with the patient's breathing effort.

The effort determined by the methods and systems described herein may be represented in any suitable way. For example, breathing effort may be represented graphically in which changes in features of the breathing band and of neighboring bands are represented by changes in color or pattern.

Alternatively, or in combination with the graphical representation, a quantitative value indicative of the relative change in effort or of an absolute value of effort may be calculated according to any suitable metric.

In addition, thresholds may be set to trigger alarms if effort increases (e.g., by percent change or absolute value) over the threshold.

In one embodiment, the present disclosure may be used in the context of a sleep study environment to detect and/or differentiate apneic events. In an embodiment, the present disclosure may be used to monitor the effect of therapeutic intervention.

In accordance with certain possible aspects of this disclosure, a photoplethysmograph ("PPG") signal is obtained from a patient. The PPG signal is subjected to only relatively light filtering to produce a lightly filtered PPG signal. For example, this light filtering may be designed to leave most or all of the meaningful or useful patient physiological information in the resulting lightly filtered PPG signal, while preventing unhelpful noise (e.g., high frequency noise) in the PPG signal from passing through to the lightly filtered PPG signal. Output circuitry (e.g., a viewer) allows a clinician user to observe patient physiological information that is contained in the lightly filtered PPG signal.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
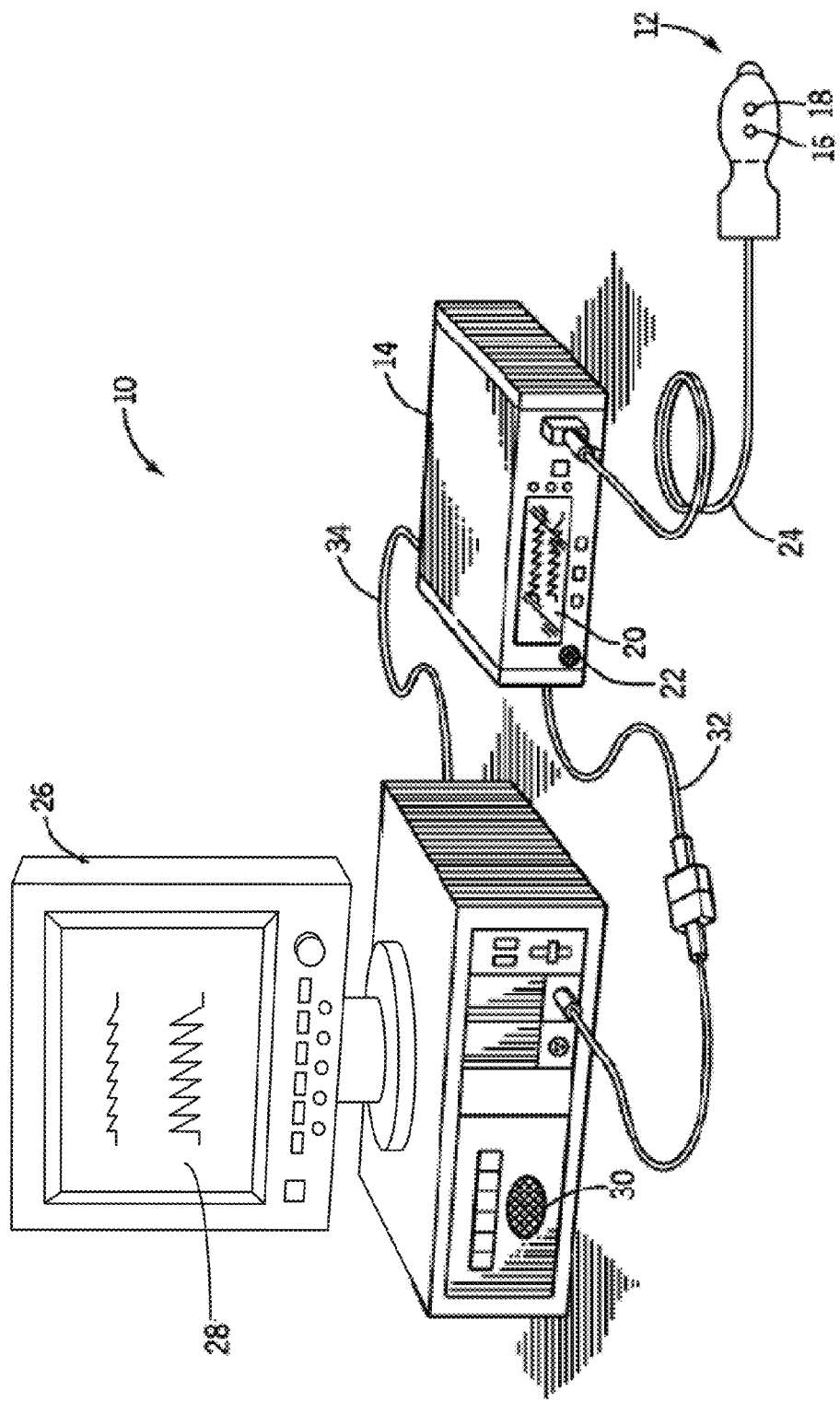
FIG. 1 shows an illustrative effort system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood. Pulse oximeters may also be used to determine respiratory effort in accordance with the present disclosure.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

(2) is then differentiated with respect to time $$\frac{d\log I}{dt} = -(s\beta_O + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_O(\lambda_R) + (1-s)\beta_r(\lambda_R)}{s\beta_O(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_O(\lambda_{IR}) - \beta_r(\lambda_{IR})) - \frac{d\log I(\lambda_{IR})}{dt}(\beta_O(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_O(\lambda_{IR}) - \beta_r(\lambda_{IR})) - \beta_O(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d \log I}{dt} = \frac{dI/dt}{I} \quad (6)$$

now (5) becomes $$\frac{\frac{d \log I(\lambda_R)}{dt}}{\frac{d \log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of an effort system 10. In an embodiment, effort system 10 is implemented as part of a pulse oximetry system. System 10 may include a sensor 12 and a monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

Sensor 12 or monitor 14 may further include, but are not limited to software modules that calculate respiration rate, airflow sensors (e.g., nasal thermistor), ventilators, chest straps, transthoracic sensors (e.g., sensors that measure transthoracic impedence).

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the effort or oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, effort system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's respiratory effort or blood oxygen saturation (referred to as an "$SpO_2$" measurement) generated by monitor 14, pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
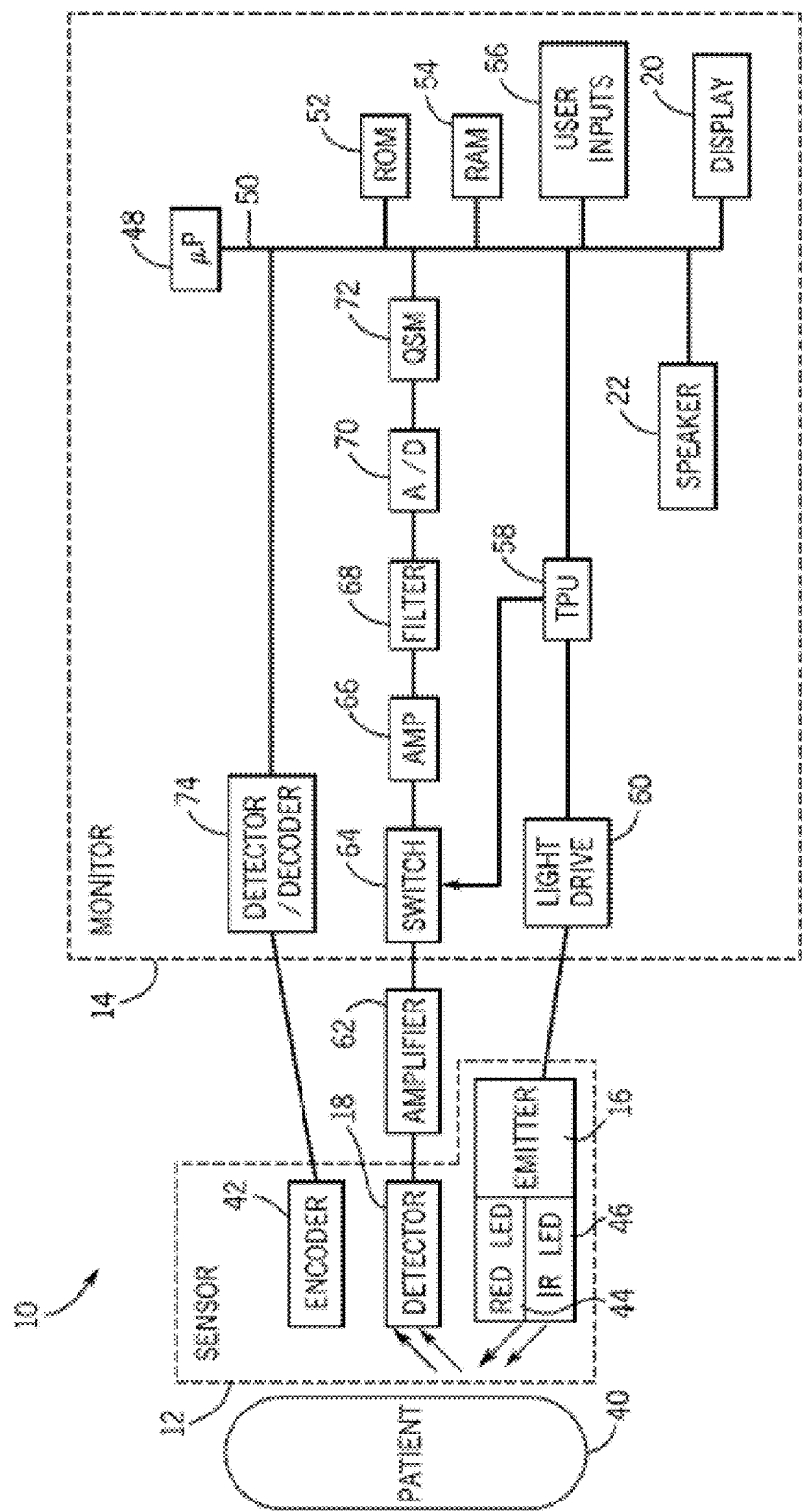
FIG. 2 is a block diagram of the illustrative effort system of FIG. 1 coupled to a patient in accordance with an embodiment.

FIG. 2 is a block diagram of an effort system, such as effort system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit one or more wavelengths of light (e.g., RED and/or IR) into a patient's tissue 40. Hence, emitter 16 may include a RED light emitting light source such as RED light emitting diode (LED) 44 and/or an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as effort, $SpO_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing effort and pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi^*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '| |' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a, b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}\left(e^{i2\pi f_0 t} - e^{-(2\pi f_0)^2/2}\right)e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
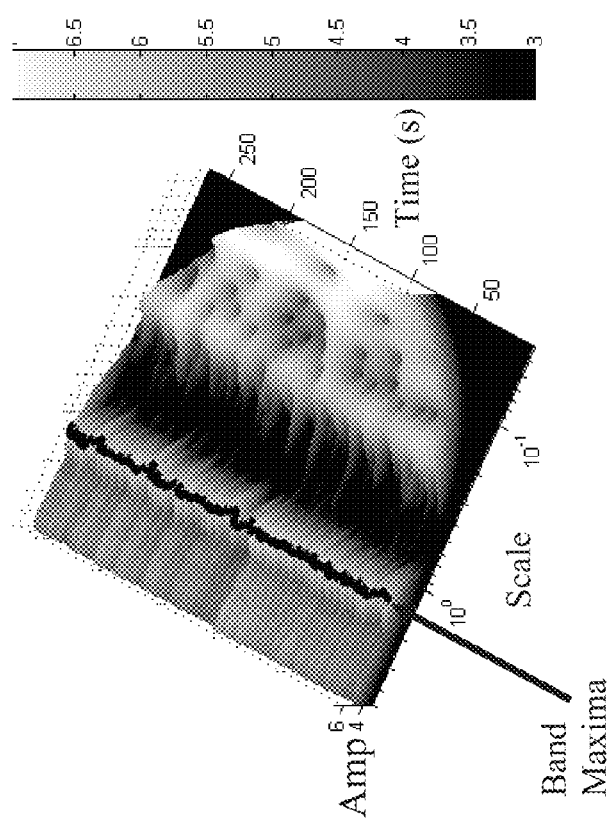
FIGS. 3(a) and 3(b) show illustrative views of a scalogram derived from a PPG signal in accordance with an embodiment.
Figure 3A:
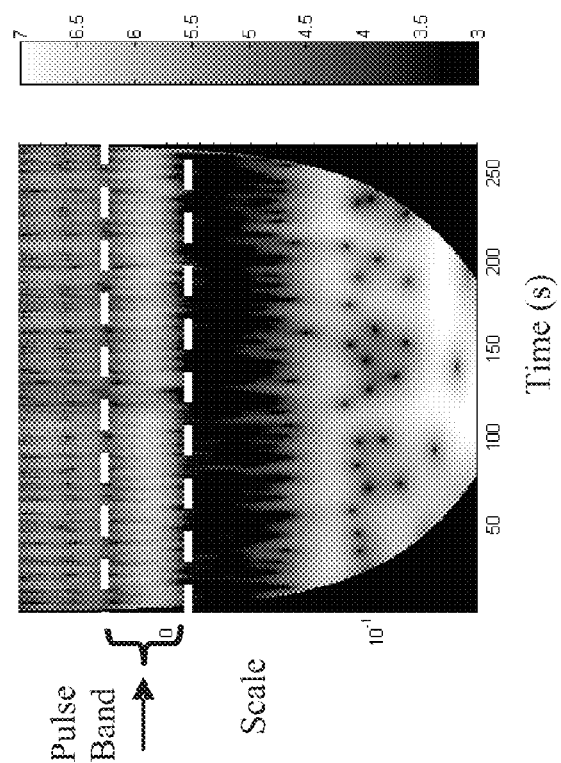

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
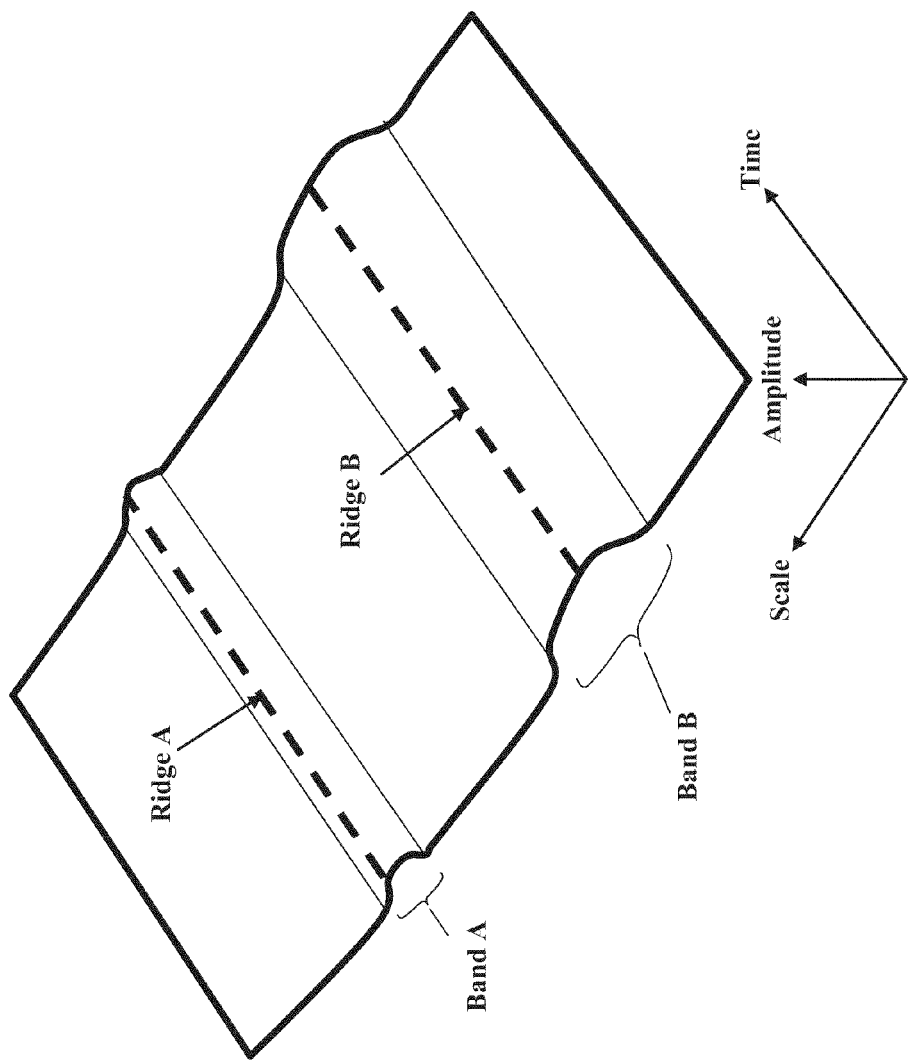
FIG. 3(c) shows an illustrative scalogram derived from a signal containing two pertinent components in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, the band ridge is defined as the locus of the peak values of these bands with respect to scale. For purposes of discussion, it may be assumed that band B contains the signal information of interest.

Figure 3D:
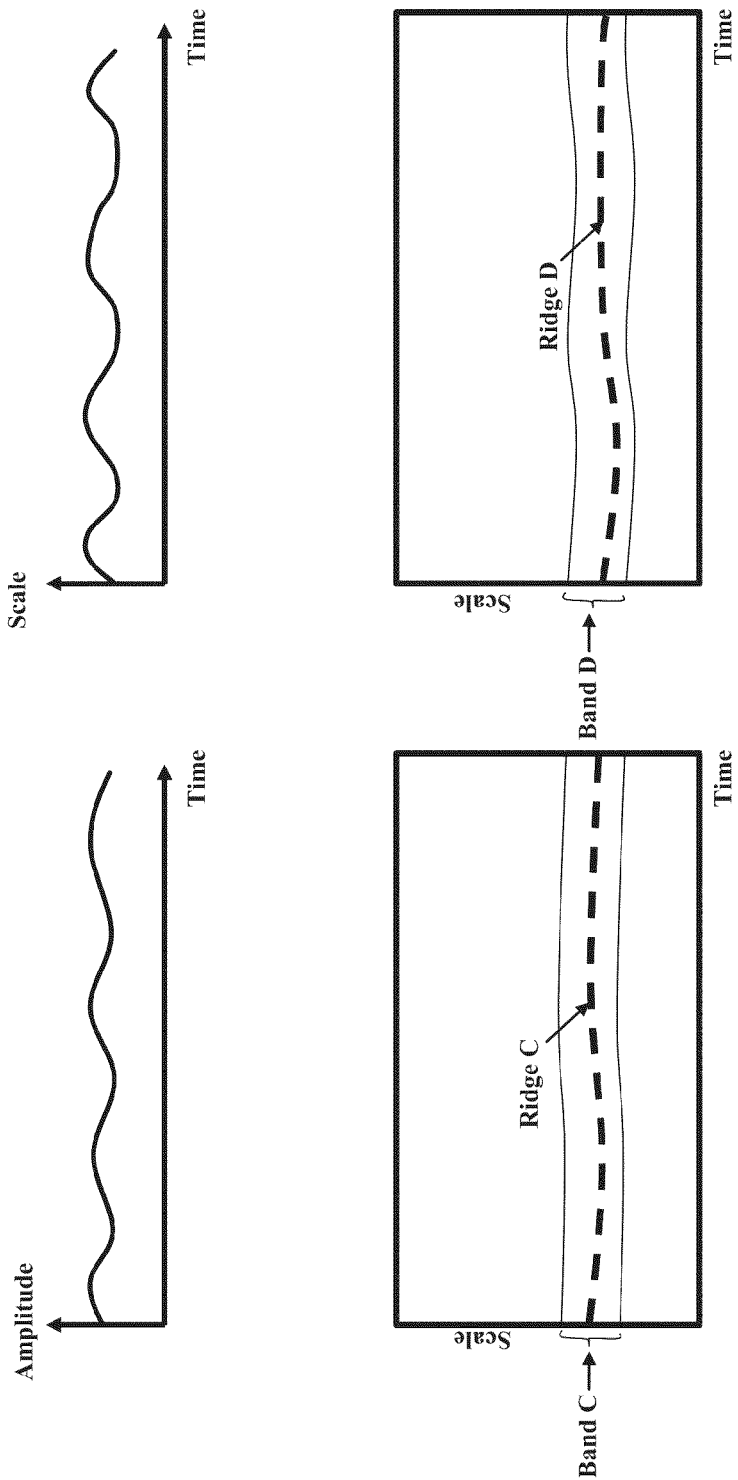
FIG. 3(d) shows an illustrative schematic of signals associated with a ridge in FIG. 3(c) and illustrative schematics of a further wavelet decomposition of these newly derived signals in accordance with an embodiment.

This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_{0}^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_{0}^{\infty} \frac{|\hat{\psi}(f)|^2}{f} df \quad (17)$$

Figure 3E:
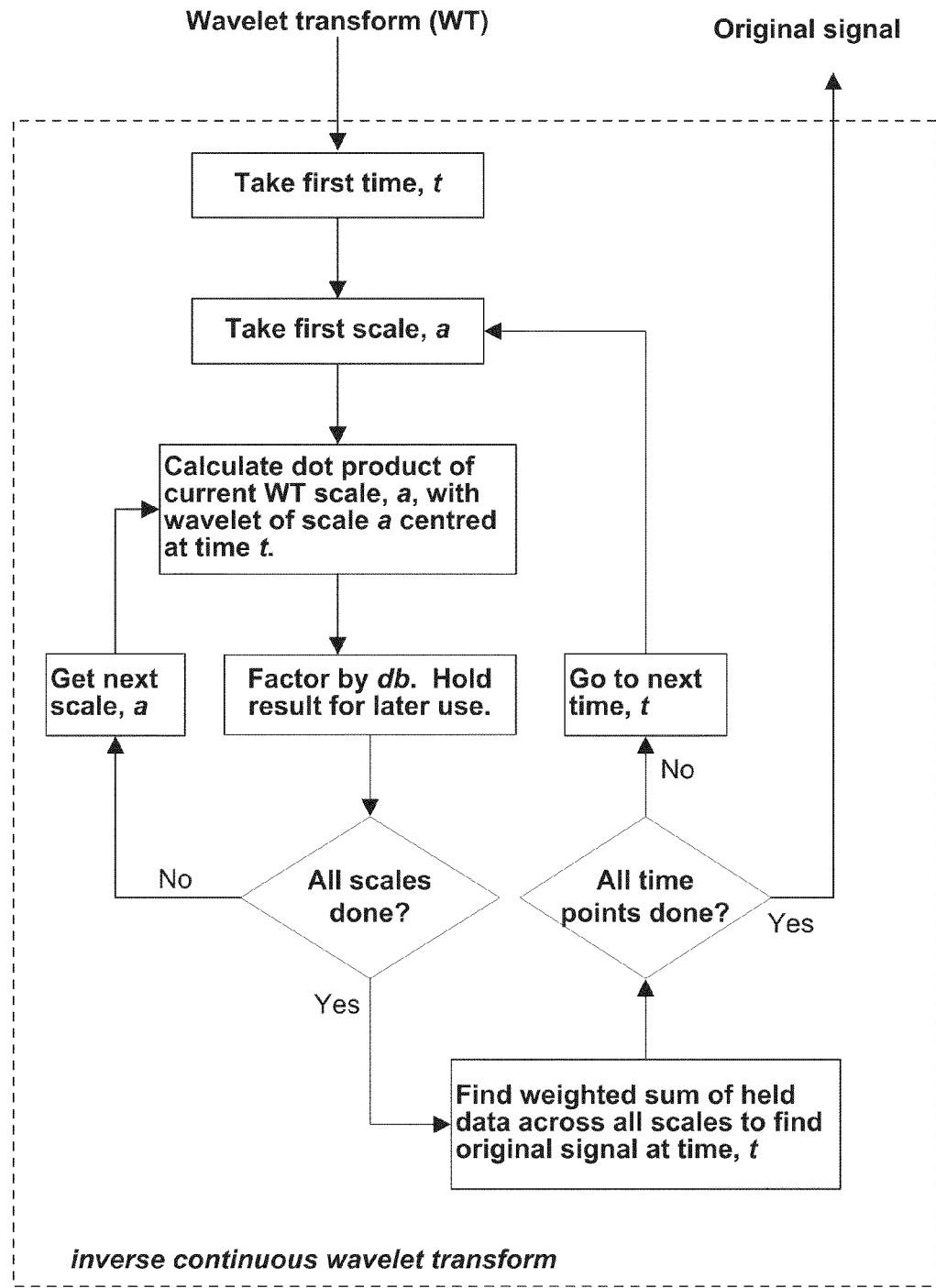
FIGS. 3(e) and 3(f) are flow charts of illustrative steps involved in performing an inverse continuous wavelet transform in accordance with embodiments.
Figure 3F:
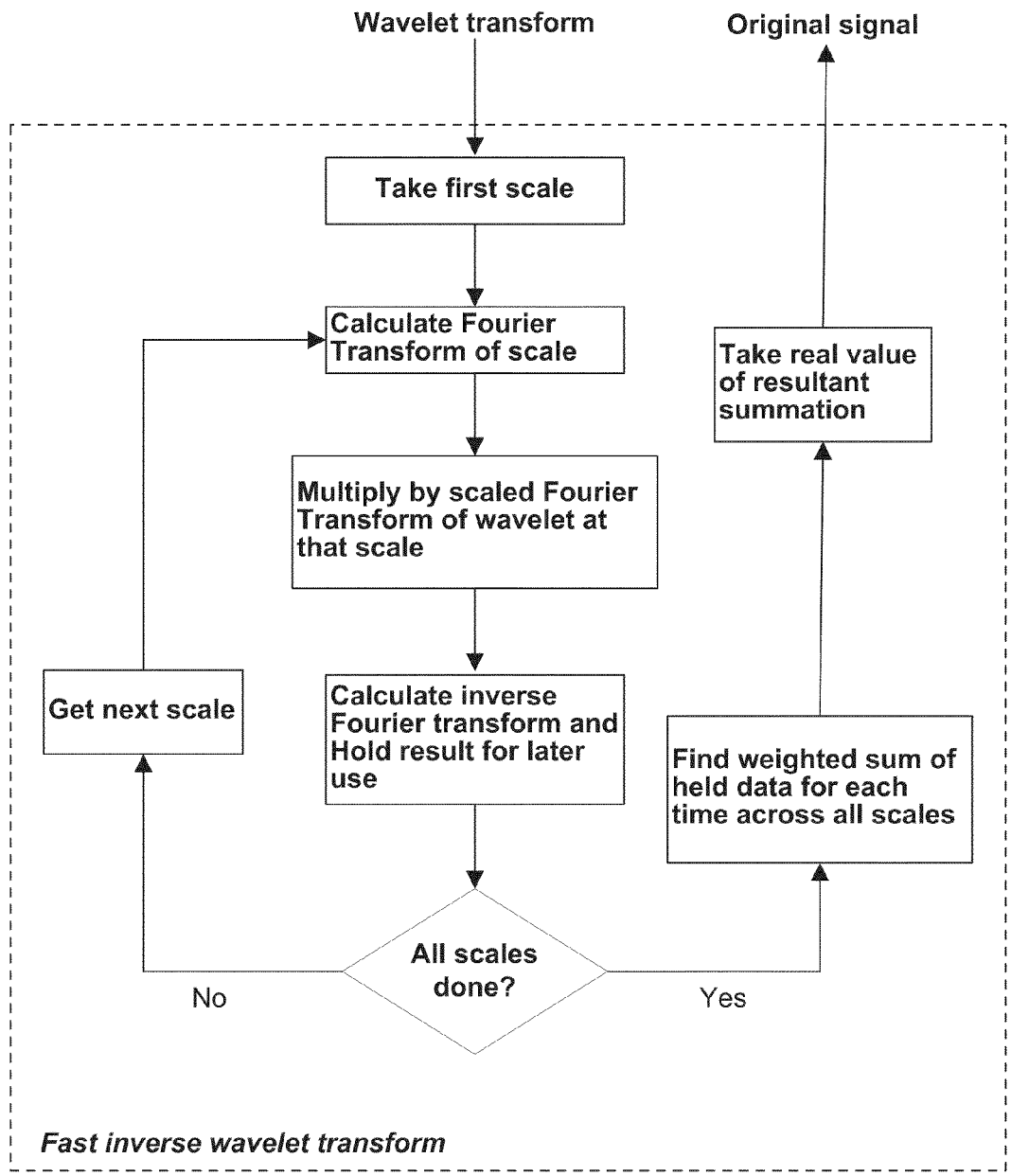

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for processing a signal using the above mentioned techniques and analyzing the results of the techniques to determine effort. In one embodiment, effort may relate to a measure of strength of at least one repetitive feature in a signal. In another embodiment, effort may relate to physical effort of a process that may affect the signal (e.g. effort may relate to work of a process). For example, effort calculated from a PPG signal may relate to the respiratory effort of a patient. Respiratory effort may increase, for example, if a patient's respiratory pathway becomes restricted or blocked. Conversely, respiratory effort may decrease as a patient's respiratory pathway becomes unrestricted or unblocked. The effort of a signal may be determined, for example, by transforming the signal using a wavelet transform and analyzing features of a scalogram derived from the wavelet transform. In particular, changes in the features of the pulse band and breathing band in the scalogram may be correlated to a change in breathing effort.

As an additional example, the methods and systems disclosed herein may be used to determine effort in a mechanical engine. Over time, a mechanical engine may become less efficient because of wear of the mechanical parts and/or insufficient lubrication. This may cause extra strain on the engine parts and, in particular, cause the engine to exert more effort, work, or force to complete a process. Engine function may be monitored and represented using signals. These signals may be transformed and analyzed to determine effort using the techniques described herein. For example, an engine may oscillate in a particular manner. This oscillation may produce a band or bands within a scalogram. Features of this band or bands may change as the engine exerts more or less effort. The change in the features may then be correlated to effort.

It will be understood that the present disclosure is applicable to any suitable signals and that PPG signals or mechanical monitoring signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

The methods for determining effort described in this disclosure may be implemented on a multitude of different systems and apparatuses through the use of human-readable or machine-readable information. For example, the methods described herein maybe implemented using machine-readable computer code and executed on a computer system that is capable of reading the computer code. An exemplary system that is capable of determining effort is depicted in FIG. 4.

Figure 4:
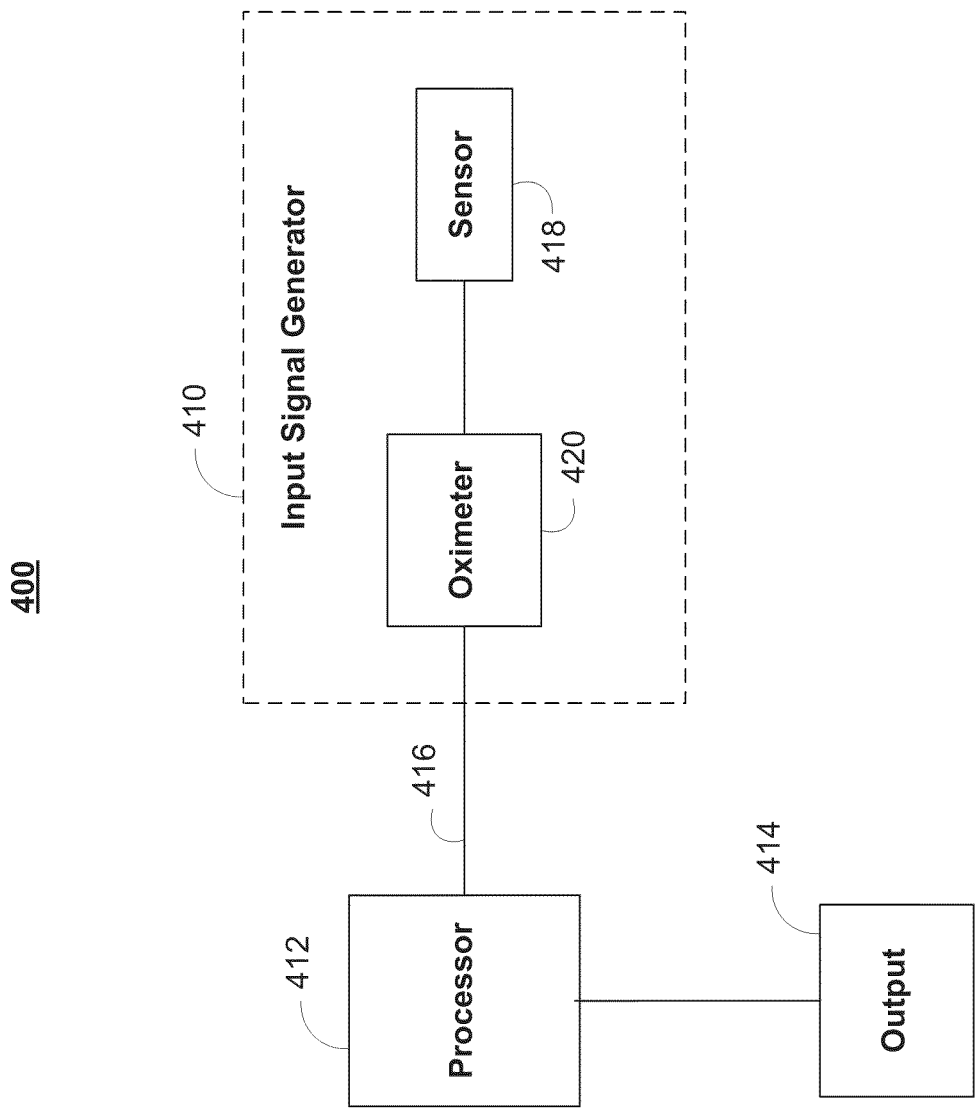
FIG. 4 is a block diagram of an illustrative continuous wavelet processing system in accordance with some embodiments.

FIG. 4 is an illustrative continuous wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In some embodiments, in order to determine effort, processor 412 may first transform the signal into any suitable domain, for example, a Fourier, wavelet, spectral, scale, time, time-spectral, time-scale domains, or any transform space. Processor 412 may further transform the original and/or transformed signals into any of the suitable domains as necessary.

Processor 412 may represent the original or transformed signals in any suitable way, for example, through a two-dimensional representation or three-dimensional representation, such as a spectrogram or scalogram.

After processor 412 represents the signals in a suitable fashion, processor 412 may then find and analyze selected features in the signal representation of signal 416 to determine effort. Selected features may include the value, weighted value, or change in values with regard to energy, amplitude, frequency modulation, amplitude modulation, scale modulation, differences between features (e.g., distances between ridge amplitude peaks within a time-scale band).

For example, selected features may include features in a time-scale band in wavelet space or a rescaled wavelet space described above. As an illustrative example, the amplitude or energy of the band may be indicative of the breathing effort of a patient when the band is the patient's breathing band. Furthermore, changes in the amplitude or energy of the band may be indicative of a change in breathing effort of a patient. Other time-scale bands may also provide information indicative of breathing effort. For example, amplitude modulation, or scale modulation of a patient's pulse band may also be indicative of breathing effort. Effort may be correlated with any of the above selected features, other suitable features, or any combination thereof.

The selected features may be localized, repetitive, or continuous within one or more regions of the suitable domain space representation of signal 416. The selected features may not necessarily be localized in a band, but may potentially be present in any region within a signal representation. For example, the selected features may be localized, repetitive, or continuous in scale or time within a wavelet transform surface. A region of a particular size and shape may be used to analyze selected features in the domain space representation of signal 416. The region's size and shape may be selected based at least in part on the particular feature to be analyzed. As an illustrative example, in order to analyze a patient's breathing band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. For example, the expected locations may be based at least in part on empirical data of a plurality of patients. The region may also be selected based at least in part on patient classification. For example, an adult's breathing band location generally differs from the location of a neonatal patient's breathing band. Thus, the region selected for an adult may be different than the region selected for a neonate.

In some embodiments, the region may be selected based at least in part on features within a scalogram. For example, the scalogram for a patient may be analyzed to determine the location of the breathing band and its corresponding ridge. The breathing band ridge may be located using standard ridge detection techniques. Ridges may also be detected using the techniques described in Watson et al., U.S. application Ser. No. 12/245,326, filed Oct. 3, 2008, entitled "Systems and Methods for Ridge Selection in Scalograms of Signals," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, the region may be determined based at least in part on the repetitive nature of the selected features. For example, a band may have a periodic feature. The period of the feature may be used to determine bounds of the region in time and/or scale.

The size, shape, and location of the one or more regions may also be adaptively manipulated using signal analysis. The adaptation may be based at least in part on changing characteristics of the signal or features within the various domain spaces.

As a signal is being processed, for example by processor 412, the region may be moved over the signal in any suitable domain space over any suitable parameter in order to determine the value or change in value of the selected features. The processing may be performed in real-time or via a previously recorded signal. For example, a region may move over the breathing band in the time-scale domain over time. When the selected features have been analyzed, they may be correlated with effort over time, and hence show the value or change in value of effort over time.

In some embodiments, the determined effort may be provided as a quantitative or qualitative value indicative of effort. The quantitative or qualitative value may be determined using the value or change in values in one or more suitable metrics of relevant information, such as the selected features mentioned above. The quantitative or qualitative values may be based on an absolute difference from a baseline or a calibrated value of the features. For example, breathing effort of a patient may be calibrated upon initial setup. Alternatively, the values may be indicative of a relative change in the features such as the change in distance between peaks in amplitude, changes in magnitude, changes in energy level, or changes in the modulation of features.

The quantitative or qualitative value of effort may be provided to be displayed on a display, for example on display 28. Effort may be displayed graphically on a display by depicting values or changes in values of the determined effort or of the selected features described above. The graphical representation may be displayed in one, two, or more dimensions and may be fixed or change with time. The graphical representation may be further enhanced by changes in color, pattern, or any other visual representation.

The depiction of effort through a graphical, quantitative, qualitative representation, or combination of representations may be presented on output 414 and may be controlled by processor 412.

In some embodiments, a display and/or speaker on output 414 may be configured to produce visual and audible alerts, respectively, when effort rises above or falls below some quantitative or qualitative threshold value. Visual alerts may be displayed on, for example, display 28 and audible alerts may be produced on, for example, speaker 22. The threshold value may be based at least in part on empirical data, baseline readings, average readings, or a combination of data. The threshold value may be configured at the start of operation or configured during operation. In some embodiments, processor 412 may determine whether or not to produce visual, audible, or combination of alerts. The alerts may be triggered if effort rises above or falls below the threshold value by a particular percentage change or absolute value change.

The analysis performed above that leads to a value of determined effort and/or an alert may also be used to detect events based at least in part on determined effort and/or other detected features. For example, this process may be used in connection with sleep studies. Increased effort may be used to detect and/or differentiate apneic events from other events. For example, reduced effort may indicate a central apnea and increased effort may indicate an obstructive apnea. In an embodiment, respiration effort from a PPG signal may be used in combination with other signals typically used in sleep studies. In one embodiment, the present disclosure may be used to monitor the effect of therapeutic intervention, for example, to monitor the effect of asthmatic drugs on a patient's respiratory effort. For example, a patient's respiratory effort may be monitored to determine how quickly the patient's respiratory effort reduces over time, if at all, after the patient receives a drug to relieve the symptoms of asthma.

Figure 5:
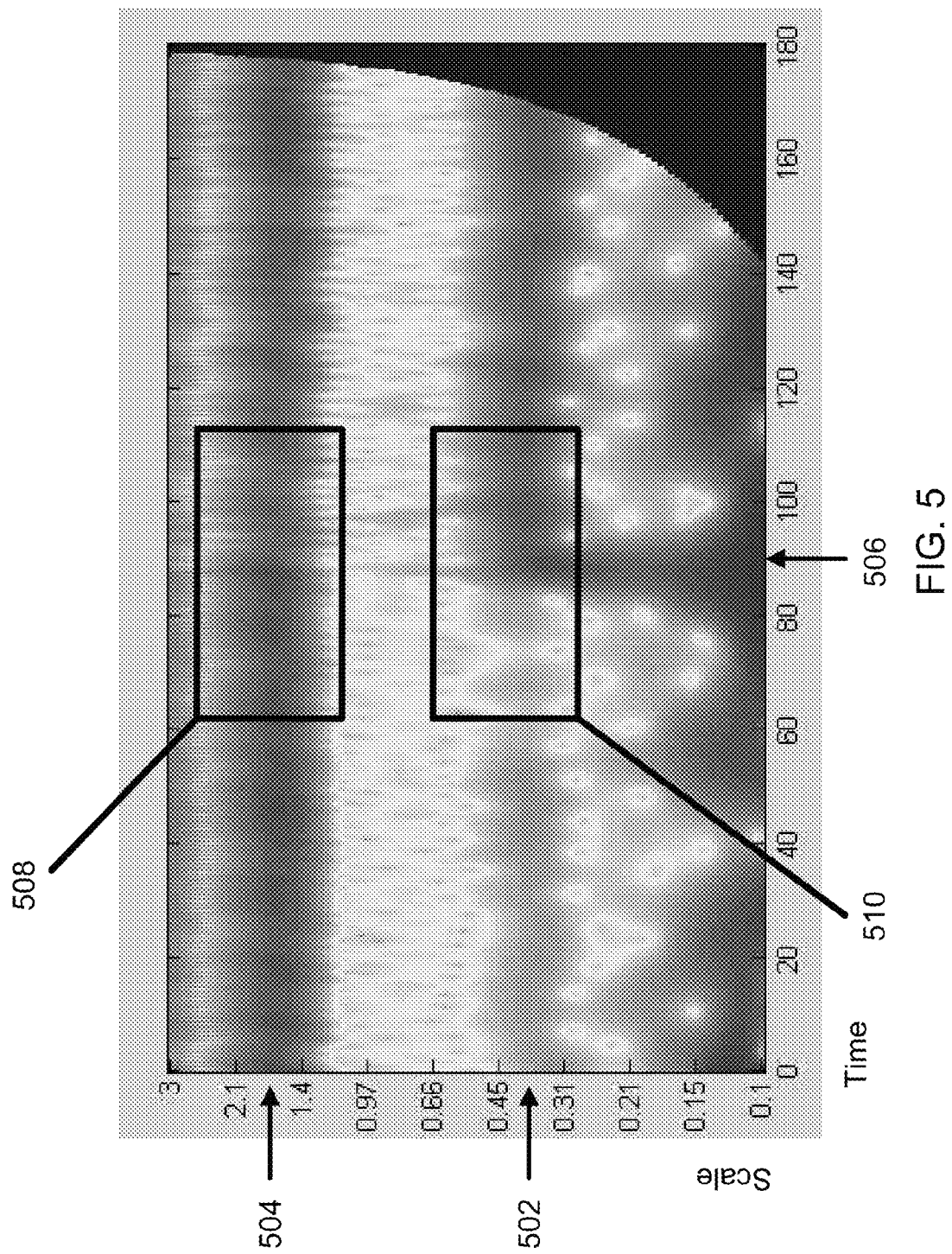
FIG. 5 is an illustrative scalogram showing the manifestation of a plurality of bands and an increase in effort in accordance with some embodiments.

FIG. 5 shows an illustrative scalogram of a PPG signal that may be analyzed in accordance with an embodiment of the disclosure. The scalogram may be produced by system 10 of FIGS. 1 and 2 or system 400 of FIG. 4 as described above. The scalogram as shown includes breathing band 502 and pulse band 504. These bands may be found and analyzed for features that may be indicative of breathing effort.

FIG. 5 shows an increased respiratory effort beginning at time 506, which may be caused by a patient experiencing increased breathing resistance. In order to detect this change in respiration effort, regions 508 and 510 may be used. Region 508 is generally located over a portion of pulse band 504 and region 510 is generally located over a portion of breathing band 502. Regions 508 and 510 may be shifted across the scalogram over time, allowing the features within the regions to be analyzed over time. The size, shape, and locations of regions 508 and 510 are merely illustrative. The features of the regions may be changed as they are shifted and any other suitable size, shape, and location may be used as described above.

At time 506, it may be observed that the modulation of the amplitude and scale of pulse band 504 may begin to increase (e.g., within region 508). Analysis of this modulation or change of this modulation, as described above, may be correlated to the patient's breathing effort because increased respiration effort may lead to this increase in amplitude and scale modulation of the pulse band. The modulation may be determined by analyzing, for example, the modulation of the ridge of the pulse band.

Increased respiration effort may also lead to increased amplitude and energy of the breathing band 502. The increase in amplitude and energy can be seen within region 510 at time 506. The amplitude may be determined by analyzing the ridge of the respiration band. The energy may be determined by analyzing the average or median energy within region 510. Analysis of the amplitude and/or energy or change in amplitude and/or energy within region 510 may also be correlated to the patient's breathing effort.

The patient's breathing effort may be determined based at least in part on the amplitude modulation, scale modulation, the amplitude, or the energy of the respiration band or the pulse band, or changes in those features, or any suitable combination thereof.

It will be understood that the above techniques for analyzing a patient's breathing effort can be used to determine any kind of effort. For example, these techniques can be used to determine the effort associated with any biological process, mechanical process, electrical process, financial process, geophysical process, astronomical process, chemical process, physical process, fluid process, speech process, audible process, meterological process, and/or any other suitable process, and/or any combination thereof.

As an additional example, the above techniques may be used to determine effort in a mechanical engine. Engine function may be monitored and represented using signals. These signals may be transformed and represented by, for example, a scalogram. Normal engine function may produce a band or bands within the scalogram. Features of this band or bands may change or become apparent as the engine exerts more or less effort. These features may include changes in the amplitude modulation, scale modulation, the amplitude, or energy of the bands. These features may also change or become apparent in other regions of the scalogram. The appearance or change in these features may then be correlated to effort or change in effort exerted by the engine.

It will also be understood that the above techniques may be implemented using any human-readable or machine-readable instructions on any suitable system or apparatus, such as those described herein.

Figure 6:
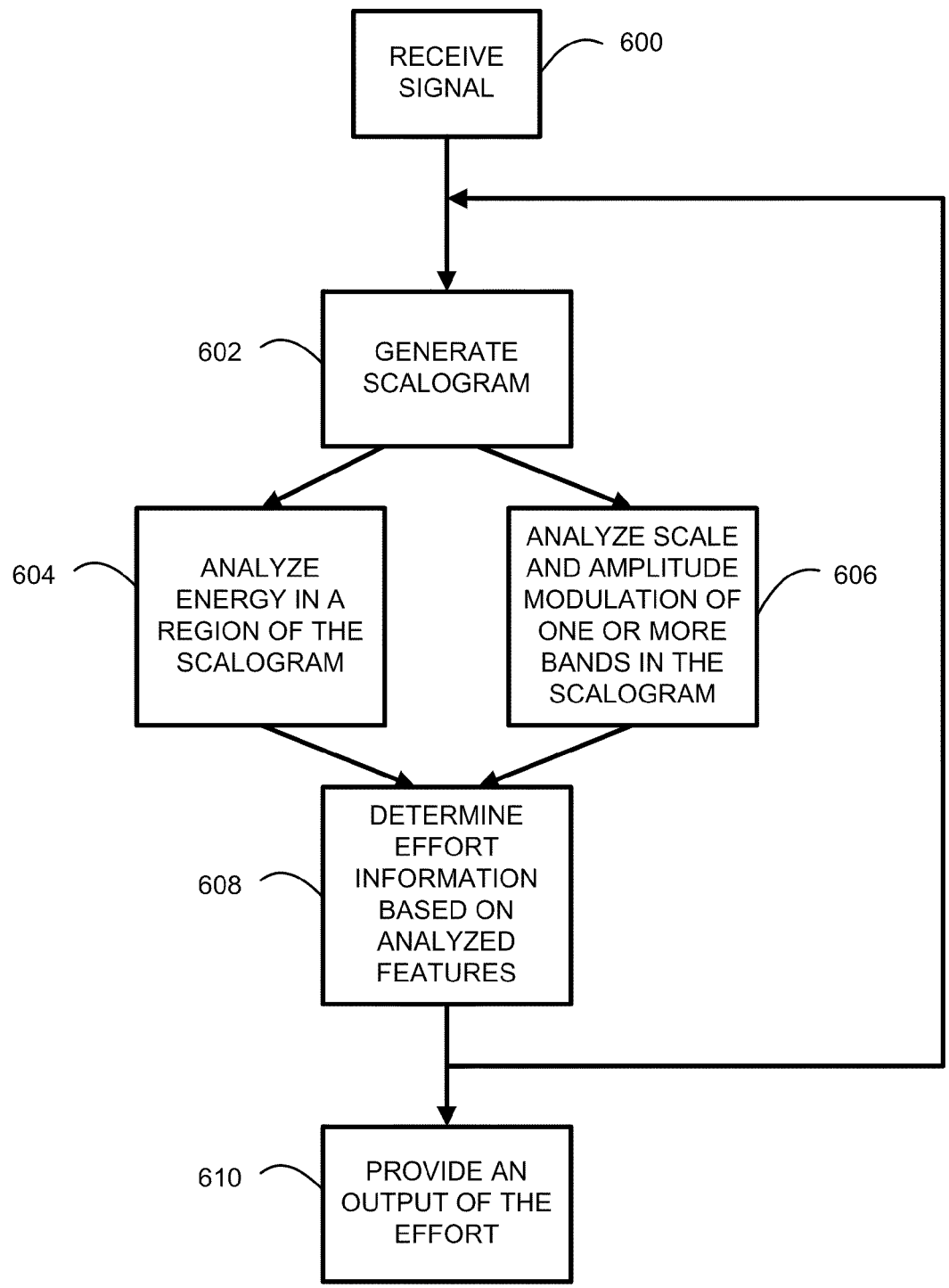
FIG. 6 is an illustrative flow chart depicting the steps used to determine effort in accordance with some embodiments.

FIG. 6 is an illustrative flow chart depicting the steps that may be used to determine effort. In step 600, one or more signals may be received, including, for example, one or more biosignals (e.g., electrocardiogram, electroencephalogram, electrogastrogram, electromyogram, heart rate signals, pathological sounds, ultrasound, or any other suitable biosignal), physiological signals, dynamic signals, non-destructive testing signals, condition monitoring signals, fluid signals, geophysical signals, physical signals, astronomical signals, electrical signals, electromagnetic signals, mechanical signals, financial signals including financial indices, sound and speech signals, chemical signals, meteorological signals including climate signals, and/or any other suitable signal, and/or any combination thereof. As an illustrative example, the input signal may be a PPG signal.

In step 602, the received signal(s) may be transformed into any suitable domain, such as a Fourier, wavelet, spectral, scale, time, time-spectral, or time-scale domain. For example, the signal(s) may be transformed into a time-scale domain using a wavelet transform such as a continuous wavelet transform. Once the signal is transformed into a suitable domain, it may be depicted by a suitable representation. Suitable representations may include two-dimensional or three-dimensional representations. As an illustrative example, the signal transformed into the time-scale domain and then may be represented by a scalogram.

Once the signal is transformed and represented by a suitable representation, one or more features may be analyzed within the signal representation as shown in steps 604 and 606.

In steps 604 and 606, one or more regions within the signal representation may be chosen for inspection. These regions may be similar to region 508 and region 510. As stated above with respect to region 508 and region 510, the regions may be comprised of any suitable size, shape, and location. They also may be shifted across the scalogram over time, allowing features within the regions to be analyzed over time. For example, the regions may cover bands within a scalogram such as a pulse band or a respiration band. The regions may also cover any other suitable bands or features within the signal representation.

In step 604, the features analyzed within a region may include amplitude or energy. In step 606, amplitude modulation, scale or frequency modulation, distances between peaks, and/or any other suitable features and/or combination of features may be analyzed.

In step 608, effort information may be determined based at least in part on the analysis of the features in steps 604 and 608. As described above with respect to FIG. 5, effort may be correlated with changes or the appearance of the features found and analyzed in steps 604 and 606. For example, breathing effort may be correlated with a change or weighted change in amplitude, energy, amplitude modulation, frequency modulation, and/or scale modulation in the breathing and/or pulse bands. The correlation between effort and the analyzed features may be used to determine quantitative or qualitative values associated with effort. The determined values may, for example, indicate effort or a change of effort. The values may be determined based at least in part on an absolute or percentage difference from a baseline or calibrated value of effort. Furthermore, the values may be determined based at least in part on changes or appearance of the analyzed features within the signal representation.

The analysis performed in step 608 may also determine whether the determined effort has risen above or fallen below a threshold value. The threshold value may be based at least in part on empirical data, baseline readings, average readings, or a combination of data. The threshold value may be configured based at least in part on effort or features at the start of operation or may be adjusted during operation. If effort crosses a threshold value, an alert may be issued. In some embodiments, the alert may be triggered if effort rises above or falls below a threshold value by a particular percentage change, absolute value change, or if the determined effort value crosses the threshold value.

The analysis performed in step 608 may also detect events based at least in part on determined effort and/or other detected features. For example, this process may be used in connection with sleep studies. Increased effort may be used to detect and/or differentiate apneic events from other events. If such an apneic event occurs, an additional notification may be generated. In an embodiment, respiration effort from a PPG signal may be used in combination with other signals typically used in sleep studies.

In step 610, the signal analysis and determined effort may be output along with a possible alert if an alert has been triggered. The output may be displayed on a display, such as display 28 shown in FIG. 1. A graphical display may be generated based at least in part on the determined qualitative or quantitative values representing effort or changes in effort. The graphical representation may be displayed in one, two, or more dimensions and may be fixed or change with time. The graphical representation may be further enhanced by changes in color, pattern, or any other visual representation. Additionally, the alert may be made visual by being displayed on a display, for example display 28, or may be made through an audible sound on a speaker, for example speaker 22.

As the signal analysis and determined effort are being output in step 610, the whole process may repeat. Either a new signal may be received, or the effort determination may continue on another portion of the received signal(s). The process may repeat indefinitely, until there is a command to stop the effort determination, and/or until some detected event occurs that is designated to halt the effort determination process. For example, it may be desirable to halt effort determination after a sharp increase in breathing effort is detected.

It will also be understood that the above method may be implemented using any human-readable or machine-readable instructions on any suitable system or apparatus, such as those described herein.

From the foregoing disclosure it will be apparent how a photoplethysmograph ("PPG") signal can be derived or obtained from a human subject or patient. We turn now to consideration of various ways in which such a PPG signal can be used (possibly with other apparatus and/or signals) as part of various types of diagnostic studies or analyses of human subjects or patients. In particular, we here describe various respects in which a PPG waveform can be viewed and/or otherwise used so that any one or more of a wide range of physiological phenomena, events, occurrences, or conditions of a patient can be observed in or extracted from a PPG signal from the patient. One example of such diagnostic use is in a sleep study of a patient. In such a context the PPG signal may be part of a polysomnogram ("PSG") which is displayed on a viewer.

Traditionally, the PSG includes a variety of signals used in the analysis of sleep. These may include electroencephalogram ("EEG"), electrocardiogram ("ECG" or "EKG"), electromyogram ("EMG"), airflow, chest movement, abdomen movement, snoring, and/or other types of signals that may be useful in observing and analyzing various aspects of the condition of a patient who is sleeping and who is subject to one or more sleep disorders such as sleep apnea. Another signal that may be used in such studies is an $SpO_2$ signal, which indicates the degree of saturation of the patient's hemoglobin with oxygen as measured (typically) by pulse oximetry. For example, $SpO_2$ can be an important signal used in the analysis of apnea because the absence of airflow for a period of time may lead to a desaturation, which is indicative of an apneic event.

Figure 7:
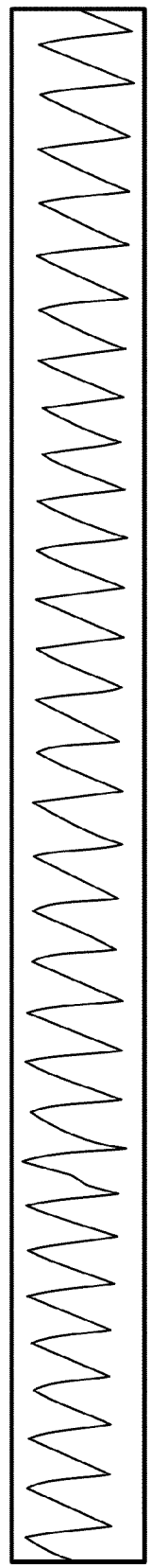
FIG. 7 is a simplified depiction of an illustrative signal waveform that is useful in explaining certain aspects of the disclosure.
Figure 8:
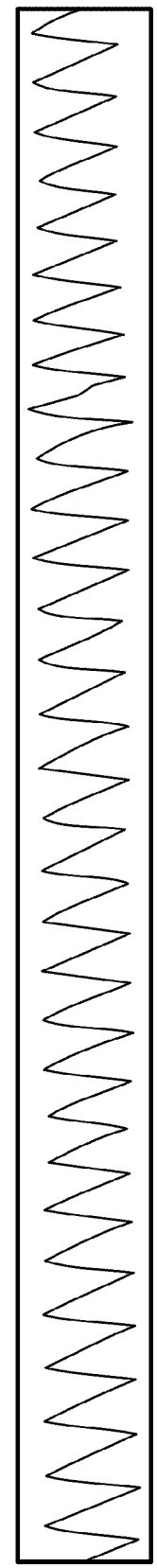
FIG. 8 is another simplified depiction of an illustrative signal waveform that is useful in explaining certain aspects of the disclosure.

In such traditional PSG studies, the PPG signal is seldom viewed. If it is used at all, this is usually done only as a visual check of the quality of the $SpO_2$ measurement. The PPG signal in this mode is typically presented exclusively in a highly filtered state, where only principal components of the patient's pulse are left after the filtering process. In this way a "text book" like PPG signal is presented to the user. For example, in such cases the PPG signal is typically band-pass filtered at or around a range of 4 Hz to 0.7 Hz. An example of such a highly filtered PPG signal is shown in FIG. 7. This is the PPG signal oriented as it is received, i.e., as a measure of light intensity. The PPG signal is often plotted inverted as shown in FIG. 8, where it is indicative of absorbance of the light through the tissue.

In accordance with certain aspects of the present disclosure, a much more lightly filtered PPG signal is employed. For example, the pass band of the filtering applied to the PPG signal may be opened out to include a wider range of signal component frequencies, while still removing very high frequency noise (and possibly also very low frequency noise) that is not useful in the analysis and that may actually inhibit the clinician viewer from interpreting the waveform. In this lightly filtered case the PPG signal may be band-pass filtered at or around a range of 4 Hz to 0.005 Hz. In an alternative embodiment the lower end of this range may be reduced even further, e.g., to 0 Hz. In this last-mentioned case, the band-pass filter becomes a low-pass filter set at or around 4 Hz. Those skilled in the art will appreciate that the frequency range of interest may be limited by or chosen on the basis of the physiological parameter(s) of interest. Thus the frequency range may alter accordingly. Further, the frequency range may change in time as the parameters being observed change. For example, dynamic or adaptive filtering may be applied.

Figure 9:
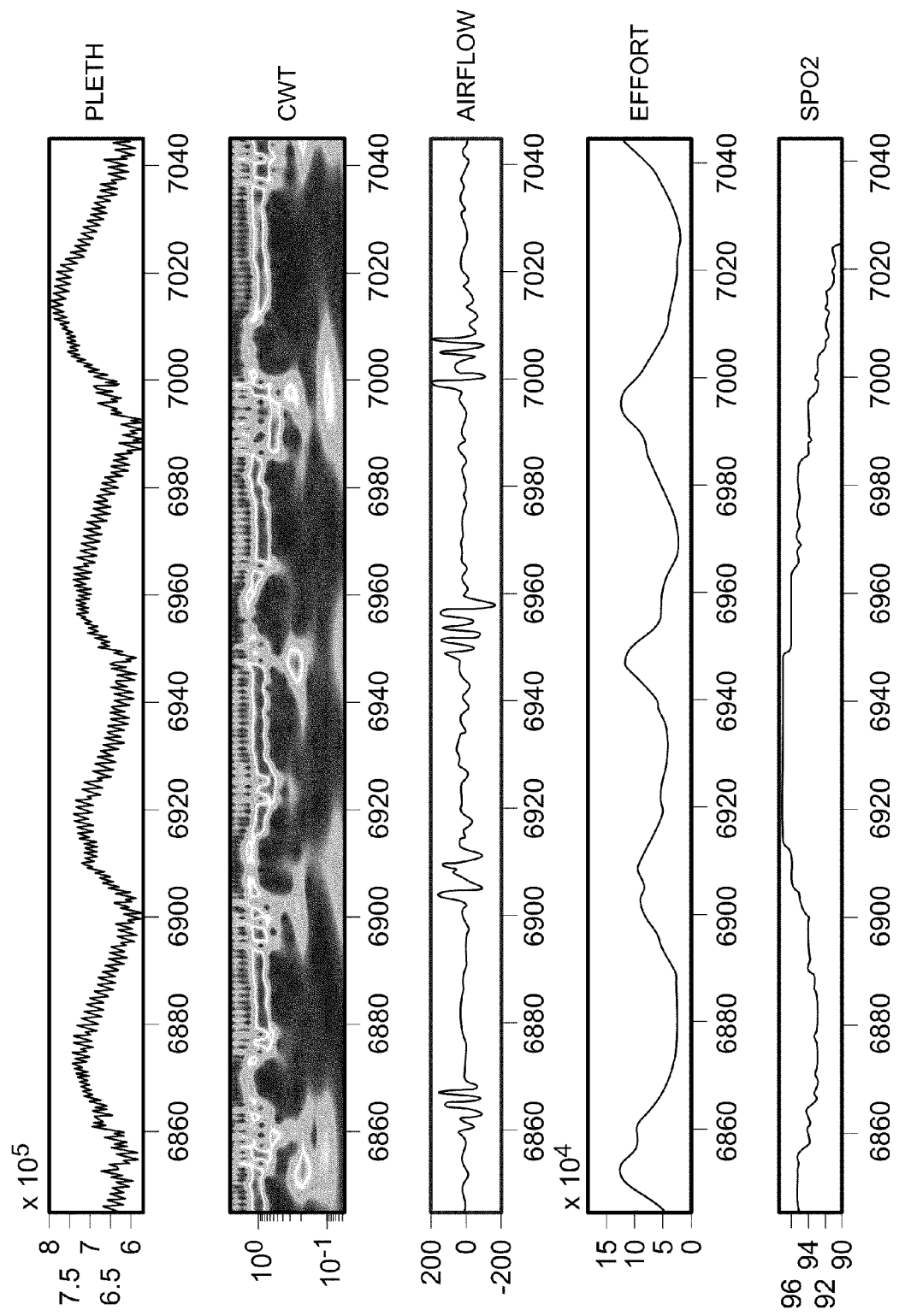
FIG. 9 is a simplified depiction of an illustrative group of signal waveforms that are useful in explaining certain aspects of the disclosure. All of the waveforms in FIG. 9 are plotted against the same horizontal time scale, and all are synchronized with one another. In other words, any particular instant of time occurs along a line that can be drawn vertically across all the waveforms in FIG. 9.

FIG. 9 shows a viewer (which can be like the viewer shown and described in Addison et al. U.S. patent application Ser. No. 12/249,046, filed Oct. 10, 2008 displaying (1) a lightly filtered PPG signal from a patient in accordance with the present disclosure in the top-most part of the viewer; (2) a scalogram of a PPG signal in the next-to-top-most part of the viewer; (3) a breathing airflow signal from the patient in the middle portion of the viewer; (4) a breathing effort signal derived from the PPG signal, e.g., as described earlier in this specification; and (5) an $SpO_2$ signal from the patient. All of the signals shown in FIG. 9 are plotted against the same horizontal time scale, and all are synchronized with one another. In other words, any given instant of time can be represented by a single line drawn vertically across all of the different signal displays in FIG. 9. Time increases to the right across FIG. 9. The lightly filtered PPG signal (top-most signal plot in FIG. 9) is oriented as a light intensity signal as described above and as shown in FIG. 7.

Figure 10:
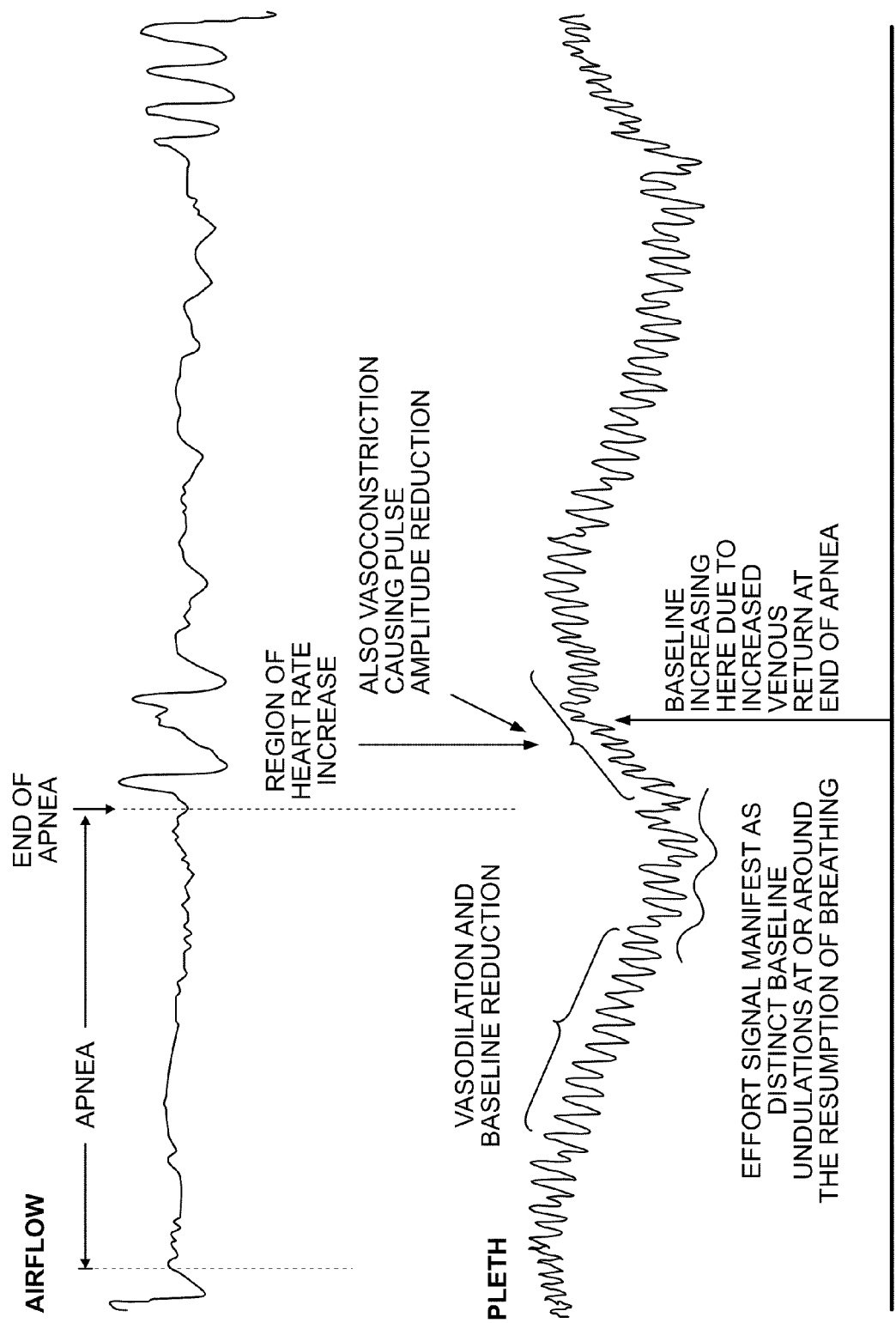
FIG. 10 is an enlargement of representative portions of two of the signal waveforms in FIG. 9. Some explanatory annotations have been added in FIG. 10. Both of the waveforms are again shown synchronized with one another in FIG. 10.

FIG. 10 shows a more detailed (enlarged) plot of a representative portion of the lightly filtered PPG signal from FIG. 9, together with the concurrent portion of the breathing airflow signal from FIG. 9. The richer morphology of this PPG signal (as compared to the more highly filtered PPG signal shown in FIG. 7) reveals hitherto hidden, clinically useful information in the FIGS. 9/10 PPG signal. From this lightly filtered PPG signal a variety of physiological information becomes available. Some examples are described in the next several paragraphs (with particular reference to FIG. 10).

Just at or before the end of the apnea (or apneic event) there is a distinct increase in respiratory effort. This is reflected (in the lightly filtered PPG signal) in the distinct baseline undulations prior to the resumption of airflow.

Just at or after the end of the apnea stage (beginning of airflow) there is a resumption of venous return. This means that venous blood is drawn from the peripheries of the patient's circulatory system and the light intensity (as indicated in the lightly filtered PPG signal) therefore increases. This can be seen as an increase in the baseline of the lightly filtered PPG signal.

Just at or after the end of an apneic event the patient's heart rate increases. This can be seen in the more rapid cycling of the lightly filtered PPG signal waveform.

Just at or after the end of an apneic event there is a distinct vasoconstriction in the patient. This may be due to such factors as the state or degree of arousal of the patient and/or the patient's body naturally trying to increase blood pressure (increased pulse rate is also a natural response of the body to increase blood pressure). This is reflected in smaller amplitude pulses in the lightly filtered PPG signal due to less range in the absorbed light attributable to the more restricted arteries of the patient.

At some point after a period of more effective breathing by the patient, the vasoconstriction stops and vasodilation occurs. This may be due to increased relaxation of the patient as the patient returns to deeper sleep. Such vasodilation may be shown by larger amplitude pulses in the lightly filtered PPG signal.

Also at some point after a period of more effective breathing following an apneic event, venous pooling tends to occur. This refers to more blood accumulating (pooling) on the venous side of the patient's capillaries. This may be reflected in the reduction of overall light intensity and therefore a reduction in the baseline value of the lightly filtered PPG signal.

Yet another physiological condition that can be determined from the lightly filtered PPG signal is the period (cycle time) of the patient's apnea. This can be determined from the time scale of repetition of the long-term undulations in the lightly filtered PPG signal.

The above physiological phenomena determinations are only illustrative of what is available from the lightly filtered PPG signal. The above determinations can be used either individually or in various combinations with one another. They can also be used in combination with other PSG signals. These various determinations can be made visually (e.g., by visual observation of the waveforms displayed by a viewer, which display may have an appearance like that of FIG. 9). Alternatively or in addition, these determinations may be made or aided by automated signal processing and analysis of signals of the kind that cause display of signal waveforms such as are shown in FIGS. 9/10. The lightly filtered PPG signal may be derived using a variety of filtering techniques, including use of wavelet transforms. In such wavelet transforms the range of the scales employed (i.e., between a maximum and a minimum) may be associated with the physiological time scales range of interest. A wavelet transform may be used to extract a variety of information from the lightly filtered PPG signal, including (for example) the strength and period (seconds per cycle) of baseline changes due to vasodilation and/or increased venous return, increases and decreases in heart rate and/or increases or decreases in pulse amplitude concurrent with vasoconstriction, etc.

Figure 11:
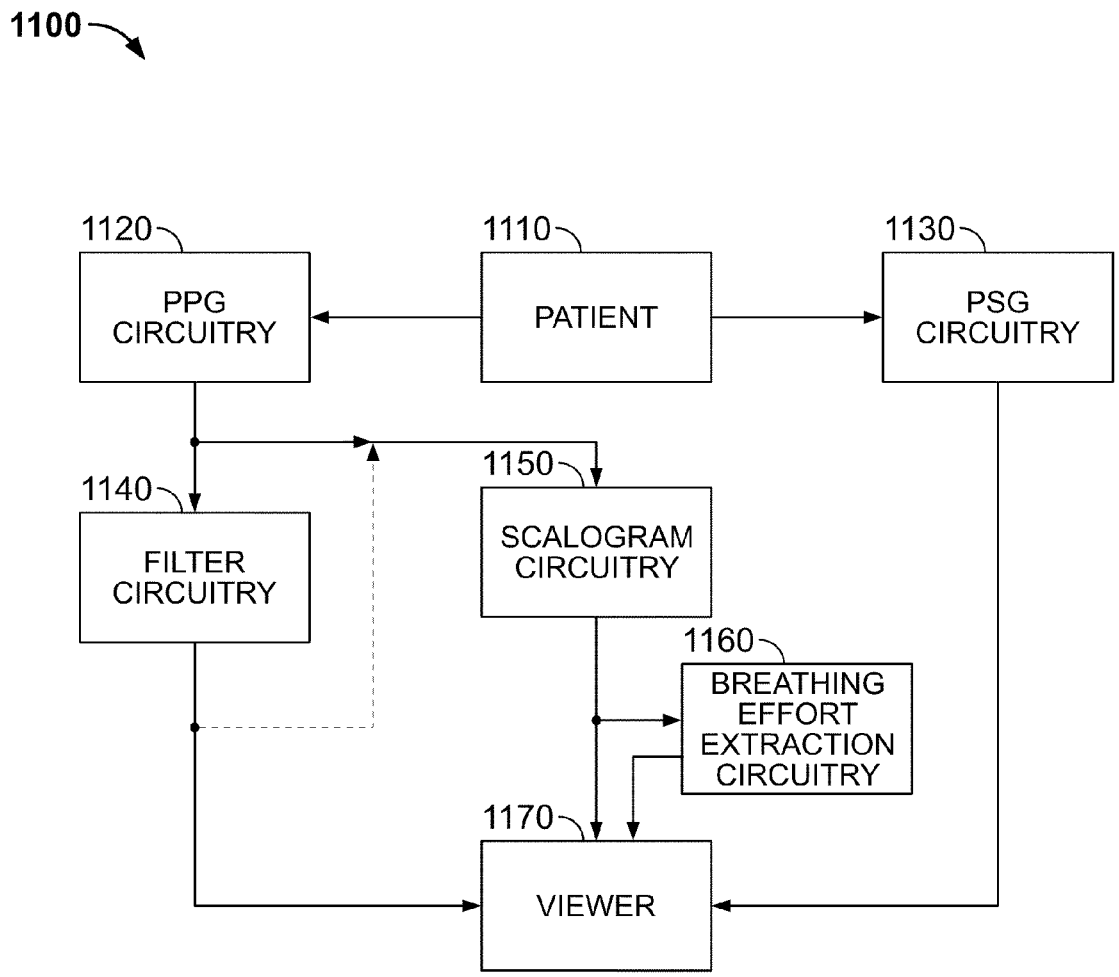
FIG. 11 is a simplified block diagram of an illustrative embodiment of apparatus constructed in accordance with the disclosure.

FIG. 11 shows an illustrative embodiment of apparatus 1100 constructed in accordance with this disclosure. For completeness, FIG. 11 (and certain subsequent FIGS.) includes a schematic representation of a human subject or "patient 1110," but it will be understood that the patient is not part of the apparatus of this disclosure. In this illustrative embodiment patient 1110 may be asleep during operation of the apparatus as described below.

As shown in FIG. 11, photoplethysmograph ("PPG") circuitry 1120 may be connected to patient 1110. PPG circuitry 1120 may be constructed as described earlier in this disclosure. Patient 1110 may also (optionally) be connected to other apparatus components, all referred to generically (and collectively) as polysomnogram ("PSG") circuitry 1130. Many examples of what may be included PSG circuitry 1130 are identified earlier in this disclosure (e.g., EEG, EKG, EMG, breathing airflow monitor, chest movement monitor, abdomen movement monitor, snoring monitor, $SpO_2$ monitor, etc.). PSG circuitry 1130 may therefore include any or all of these components. (In some respects PPG circuitry 1120 may also be considered PSG circuitry, but PPG circuitry 1120 is shown separately herein for greater clarity and detail of this disclosure.)

Each component that is included in PSG circuitry 1130 outputs one or more signals indicative of the patient's condition as detected by that PSG circuit component. These signals may be applied to viewer 1170 for visual display to the clinician user of apparatus 1100. As one specific example, PSG circuitry 1130 may include breathing airflow monitor circuitry for producing an output signal indicative of the flow rate (volume per unit of time) of air the patient is inhaling or exhaling. That airflow monitor may output an airflow signal to viewer 1170 so that the viewer can display the waveform of that signal (e.g., like the middle signal trace in FIG. 9 or the upper signal trace in FIG. 10). As another specific example, PSG circuitry 1130 may include $SpO_2$ monitor circuitry so that viewer 1170 can display a waveform of the patient's $SpO_2$ physiological condition (e.g., as in the bottom-most signal trace in FIG. 9). As mentioned earlier in this disclosure, viewer 1170 may be as shown in the above-mentioned Addison et al. Ser. No. 12/249,046 reference.

Returning now to PPG circuitry 1120, that circuitry outputs a PPG signal indicative of light intensity passing through a selected portion of the patient's body tissue. (As mentioned earlier, the PPG signal may alternatively be indicative of light absorbance by that tissue, but for simplicity of discussion only the light intensity example will generally be referred to in what follows.) In accordance with the present disclosure, the PPG signal output by PPG circuitry 1120 is applied to filter circuitry 1140, which performs the above-described "light" filtering of that signal to produce the above-described "lightly filtered PPG signal" for application to viewer 1170. (For the avoidance of any doubt or uncertainty on this point, we note that in this context the word "light" is used as the opposite of "heavy." "Light" in this context does not refer to visible electro-magnetic radiation, also known as visible light.) Viewer 1170 may visibly display the waveform of the lightly filtered PPG signal (e.g., as in the top signal trace in FIG. 9 or the bottom signal trace in FIG. 10).

The PPG signal (or alternatively the lightly filtered PPG signal (see dotted line in FIG. 11)) may also be applied to scalogram circuitry 1150. Scalogram circuitry 1150 may be circuitry as described earlier in this specification for generating a scalogram of the PPG signal. Scalogram circuitry 1150 may apply the resulting scalogram signals to viewer 1170 so that the viewer can visibly display the scalogram to the clinician user of apparatus 1100 (e.g., as in the portion of FIG. 9 just below the top-most lightly filtered PPG signal waveform trace).

The scalogram signal(s) output by scalogram circuitry 1150 may also be applied to breathing effort extraction circuitry 1160. This may be circuitry as described earlier in this disclosure for extracting from the scalogram information indicative of the effort the patient is exerting or expending in order to breathe. The resulting breathing effort signal that is output by circuitry 1160 may be applied to viewer 1170 so that the viewer can display the waveform of that signal (e.g., as in the next-to-bottom-most signal trace in FIG. 9).

Figure 12:
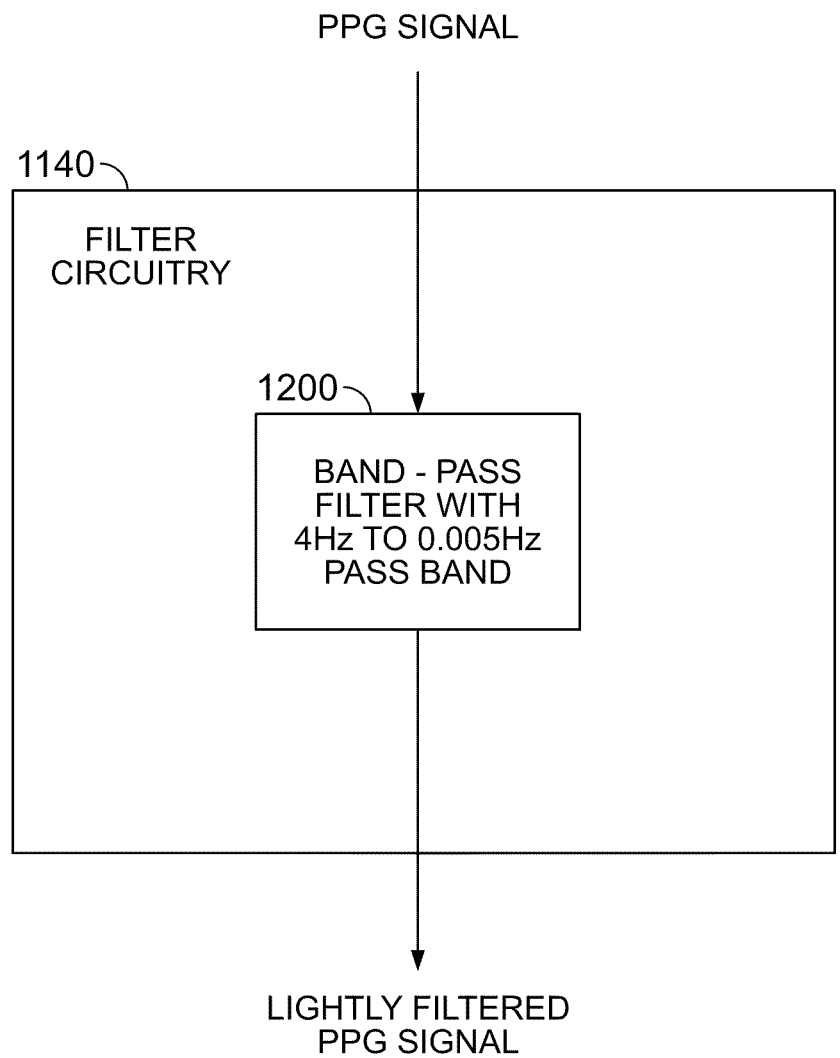
FIG. 12 is a simplified block diagram of an illustrative embodiment of how one component of the FIG. 11 apparatus can be constructed in accordance with the disclosure.

An illustrative embodiment of the construction of filter circuitry 1140 is shown in FIG. 12. In this embodiment, filter circuitry 1140 comprises a low-pass filter 1200 having a pass band between 4 Hz and 0.005 Hz. In other words, filter 1200 passes to its output (i.e., the lightly filtered PPG signal) components of the PPG signal having frequency in the range between about 4 cycles per second ("Hz") and 0.005 Hz. Filter 1200 blocks (i.e., does not pass to its output) components of the PPG signal having frequency higher than about 4 Hz or lower than about 0.005 Hz.

Figure 13:
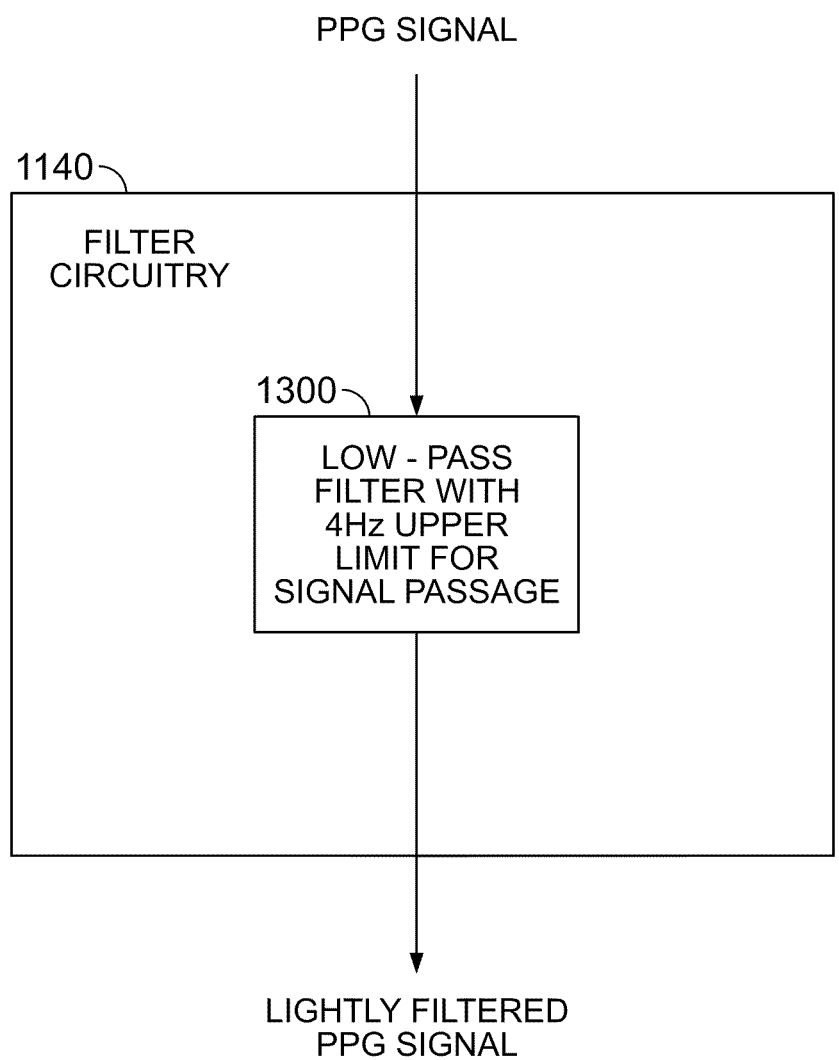
FIG. 13 is a simplified block diagram of another illustrative embodiment of how the FIG. 12 component can be constructed in accordance with the disclosure.

Another illustrative embodiment of the construction of filter circuitry 1140 is shown in FIG. 13. In this embodiment, filter circuitry 1140 comprises a low-pass filter 1300 having a pass band with an upper limit of about 4 Hz. In other words, filter 1300 passes to its output (i.e., the lightly filtered PPG signal) components of the PPG signal having frequency below about 4 Hz. Filter 1300 blocks (i.e., does not pass to its output components of the PPG signal having frequency higher than about 4 Hz.

The illustrative embodiments shown in FIGS. 12 and 13 are only examples of how filter 1140 may be constructed. For example, a band-pass filter embodiment like FIG. 12 may have an upper cut-off threshold frequency somewhat higher or lower than 4 Hz and/or a lower cut-off threshold frequency somewhat higher or lower than 0.005 Hz. Similarly, a low-pass filter embodiment like FIG. 13 may have an upper cut-off threshold frequency somewhat higher or lower than 4 Hz. In all cases, however, filter 1140 is preferably designed to pass frequency components that reveal information that it is desired to extract from the resulting lightly filtered PPG signal (e.g., (1) the relatively long-term baseline changes due to vasodilation and/or increased venous return, (2) the shorter-term baseline undulations due to increased breathing effort at or around the resumption of breathing, (3) increases in heart rate and/or decreases in pulse amplitude concurrent with vasoconstriction, etc., all as indicated in various regions of FIG. 10 and described above).

Figure 14:
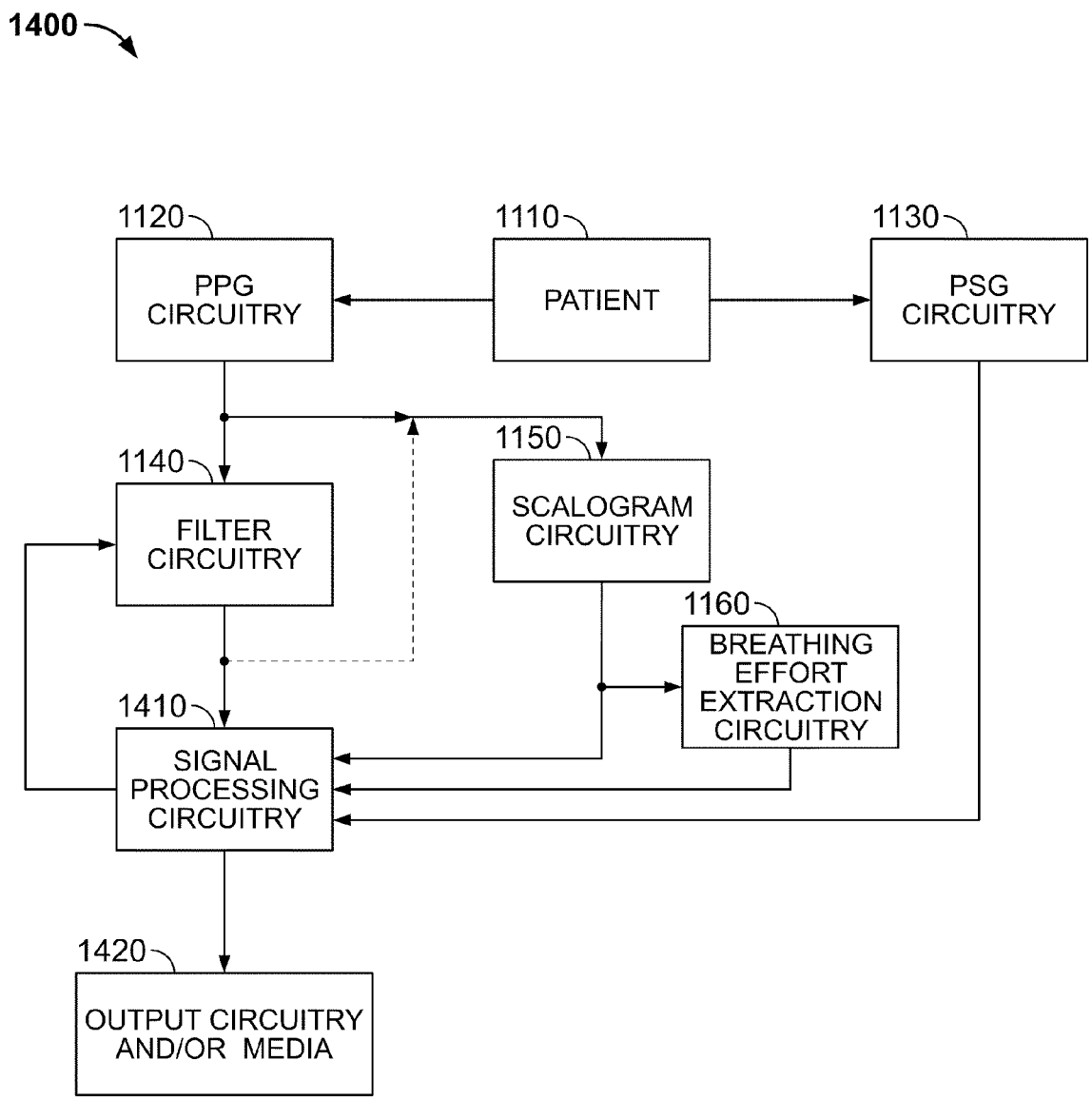
FIG. 14 is a simplified block diagram of another illustrative embodiment of apparatus constructed in accordance with the disclosure.

FIG. 14 shows another illustrative embodiment of apparatus 1400 constructed in accordance with this disclosure. Some of the elements shown in FIG. 14 can be the same as elements shown in earlier FIGS. like FIGS. 11-13. These repeated elements have the same reference numbers in all of FIGS. 11-14. Because these repeated elements have already been described in detail above, it will not be necessary to describe them again in connection with FIG. 14.

The main difference between apparatus 1400 and apparatus 1100 is that in apparatus 1400 the output signals of elements like 1130, 1140, 1150, and 1160 can be applied to signal processing circuitry 1410. This signal processing circuitry has the ability to analyze the lightly filtered PPG signal from filter circuitry 1140 (either alone or in combination with or in relation to one or more other signals from elements 1130, 1150, and/or 1160) to automatically extract one or more types of characteristics from the lightly filtered PPG signal. For example, circuitry 1410 may be able to automatically detect in the lightly filtered PPG signal a relatively long-term decrease in the signal baseline due to vasodilation in patient 1110. (See corresponding portion of the lower signal trace in FIG. 10.) As another example, circuitry 1410 may be able to automatically detect a relatively long-term increase in the baseline of the lightly filtered PPG signal due to increased venous return. (See again the corresponding portion of the lower signal trace in FIG. 10.) As still another example, circuitry 1410 may be able to automatically detect changes in the heart rate and pulse amplitude, e.g., due to vasoconstriction. (See again the corresponding portion of the lower signal trace in FIG. 10.)

Circuitry 1410 can output one or more signals indicative of the patient physiological conditions it has detected and/or extracted. The output signals of circuitry 1410 can be applied to output circuitry and/or media 1420. For example, element 1420 may be circuitry for displaying the information contained in the output signals of element 1410 (e.g., on a display monitor or by printing on paper). As another example, element 1420 may be circuitry for recording the output of element in an electronic memory, on a disc, or in or on any other suitable media for future retrieval and consideration. Element 1420 may provide both substantially immediate output of the signal information applied to it, and a recording or record of that signal information for future reference. Examples of outputs from circuitry 1410 that element 1420 may capture and/or display are information like "Baseline decreasing," "Baseline increasing," "Heart rate is [extracted value]," "Pulse amplitude is [extracted value]," a plot of the baseline vs. time, a plot of pulse rate vs. time, a plot of pulse amplitude vs. time, etc.

Figure 15:
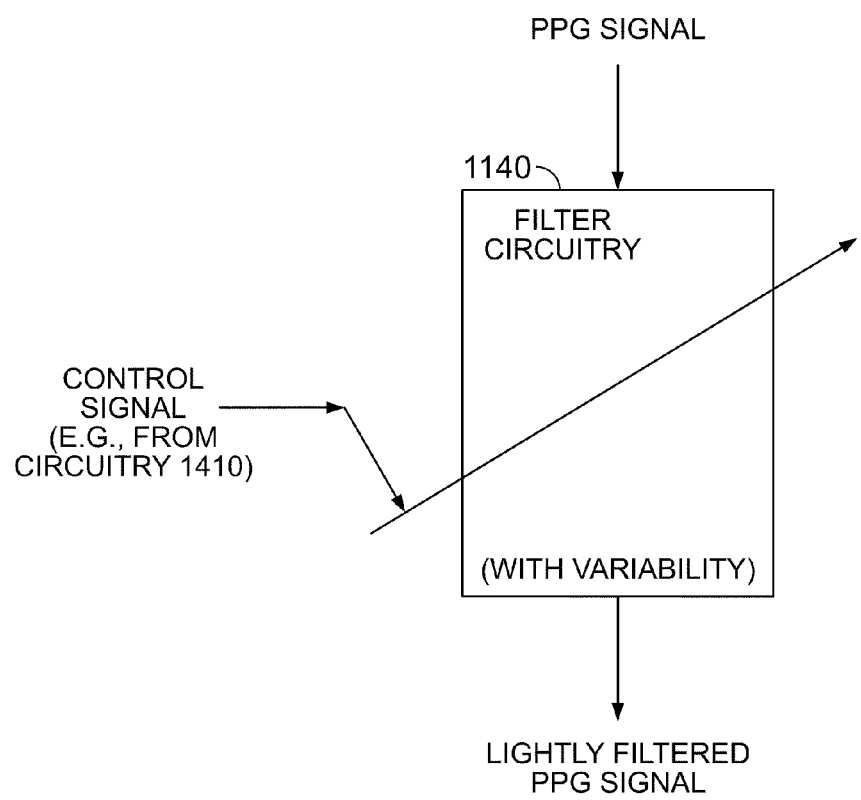
FIG. 15 is a simplified block diagram of an illustrative embodiment of how one component of the FIG. 14 (or FIG. 11) apparatus can be constructed in accordance with the disclosure.

Signal processing circuitry 1410 may also have the ability to feed back to filter circuitry 1140 signals for controlling various aspects of the operation of circuitry 1140. For example, these feedback control signals may allow element 1410 to control (i.e., automatically change) one or more of the pass/block thresholds of filter circuitry 1140. As one, more specific example of this, at a certain time, element 1410 may decrease the upper frequency limit of the pass band of filter circuitry 1140 so that only relatively long-term baseline undulations come through the filter. This may enable circuitry 1410 to more easily or more accurately analyze characteristics of the baseline. As another specific example of feedback to filter circuitry 1140, at another time, element 1410 may increase the lower frequency limit of the pass band of filter circuitry 1140 so that only relatively short-term undulations come through the filter. This may enable circuitry 1410 to more easily or more accurately analyze non-baseline characteristics of the signal output by filter 1140. FIG. 15 shows an illustrative embodiment of filter circuitry 1140 having such variability in one or more of its operating characteristics.

It will be understood that the foregoing is only illustrative of the principles of this disclosure, and that various modifications can be made by those skilled in the art without departing from the scope and spirit of the disclosure. For example, the frequency pass band or frequency pass range of the filter that produces the lightly filtered PPG signal can be varied or modified to reveal particular physiological conditions in the patient that it is desired to observe via that signal. As another example of a possible modification, output circuitry and/or media 1420 in FIG. 14 may be a viewer like viewer 1170 in FIG. 11 or may be supplemented by such a viewer. Thus signal processing as in element 1410 (and possibly also feedback from element 1410 to filter circuitry 1140) may be employed in embodiments that include a viewer 1170. The various signals referred to herein are typically electrical signals. The various circuits or circuitries referred to herein are typically electrical circuits that generate and/or process such electrical signals. For the most part, the signal traces shown and/or referred to herein are plots or displays of electrical signal waveforms, with signal amplitude shown in the vertical direction and time shown in the horizontal direction.

What is claimed is:

1. Apparatus for monitoring a physiological condition of a patient comprising:
    photoplethysmograph ("PPG") circuitry configured to obtain a PPG signal from the patient;
    filter circuitry configured to lightly filter the PPG signal to produce a lightly filtered PPG signal; and
    output circuitry configured to provide a visible display of a trace of the lightly filtered PPG signal, thereby making it possible for a clinician user of the apparatus to observe at least some patient physiological condition information contained in the lightly filtered PPG signal.

2. The apparatus defined in claim 1 wherein the filter circuitry comprises:
    a low-pass filter configured to pass components of the PPG signal having frequencies less than a threshold frequency and for blocking components of the PPG signal having frequencies greater than the threshold frequency.

3. The apparatus defined in claim 2 wherein the threshold frequency is approximately 4 Hz.

4. The apparatus defined in claim 1 wherein the filter circuitry comprises:
    a band-pass filter configured to pass components of the PPG signal having frequencies in a range between upper and lower threshold frequencies and for blocking components of the PPG signal having frequencies that are not in said range.

5. The apparatus defined in claim 4 wherein the upper threshold frequency is approximately 4 Hz.

6. The apparatus defined in claim 4 wherein the lower threshold frequency is approximately 0.005 Hz.

7. The apparatus defined in claim 1 wherein the filter circuitry has a frequency threshold at which the filter circuitry switches from passing frequency components of the PPG signal to blocking frequency components of the PPG signal, and wherein the frequency threshold is controllably variable.

8. The apparatus defined in claim 7 further comprising:
    processing circuitry configured to analyze the lightly filtered PPG signal to produce a control signal for controlling the frequency threshold.

9. The apparatus defined in claim 1 wherein the output circuitry comprises:
    processing circuitry configured to analyze the lightly filtered PPG signal to produce an output signal indicative of a physiological parameter extracted from the patient physiological condition information contained in the lightly filtered PPG signal.

10. The apparatus defined in claim 1 further comprising:
    polysomnogram ("PSG") circuitry configured to obtain a PSG signal from the patient; and wherein the output circuitry additionally makes it possible for the clinician user to observe at least some additional patient physiological condition information contained in the PSG signal.

11. The apparatus defined in claim 10 wherein the PSG circuitry comprises:
   SpO2 circuitry configured to measure saturation of the patient's hemoglobin with oxygen.

12. The apparatus defined in claim 10 wherein the PSG circuitry comprises:
   breathing airflow monitoring circuitry.

13. The apparatus defined in claim 1 further comprising:
   circuitry configured to extract from the PPG signal a breathing effort signal indicative of effort the patient is expending in order to breathe.

14. The apparatus defined in claim 13 wherein the output circuitry additionally makes it possible for the clinician user to observe the breathing effort signal.

15. The apparatus defined in claim 13 wherein the circuitry configured to extract comprises:
   circuitry configured to produce scalogram signals from the PPG signal; and
   circuitry configured to produce the breathing effort signal from the scalogram signals.

16. The apparatus defined in claim 15 wherein the output circuitry additionally makes it possible for the clinician user to observe the scalogram signals.

17. The apparatus defined in claim 1 further comprising:
   circuitry configured to produce scalogram signals from the PPG signal; and wherein the output circuitry additionally makes it possible for the clinician user to observe the scalogram signals.

18. The apparatus defined in claim 1, wherein the filter circuitry is configured to pass most or all of the patient physiological information in the PPG signal while blocking high frequency noise.

19. The apparatus defined in claim 1, wherein the filter circuitry is configured to pass principal components of the patient's pulse and lower frequency components including long-term baseline undulations of the PPG signal.

20. The apparatus defined in claim 1, wherein the filter circuitry is configured to pass low frequency baseline changes of the PPG signal that are due to vasodilation and vasoconstriction, wherein the output circuitry makes it possible for the clinician user of the apparatus to observe vasodilation and vasoconstriction information contained in the lightly filtered PPG signal.

21. A method of monitoring a physiological condition of a patient comprising:
   obtaining a photoplethysmograph ("PPG") signal from the patient;
   lightly filtering the PPG signal to produce a lightly filtered PPG signal; and
   visibly displaying a trace of the lightly filtered PPG signal so that a clinician user of the method can observe at least some patient physiological condition information that is contained in the lightly filtered PPG signal.

22. The method defined in claim 21 wherein the lightly filtering comprises:
   band-pass filtering the PPG signal with a pass band in the range from about 4 Hz to about 0.005 Hz.

* * * * *